United States Patent
Chen et al.

(10) Patent No.: US 6,537,813 B1
(45) Date of Patent: Mar. 25, 2003

(54) CONCURRENT FLOW MIXING METHODS AND APPARATUSES FOR THE PREPARATION OF GENE THERAPY VECTORS AND COMPOSITIONS PREPARED THEREBY

(75) Inventors: Xian Chen, San Diego, CA (US); Mark J. D'Andrea, Carlsbad, CA (US)

(73) Assignee: Selective Genetics, Inc., San Diego, CA (US)

(*) Notice: Subject to any disclaimer, the term of this patent is extended or adjusted under 35 U.S.C. 154(b) by 0 days.

(21) Appl. No.: 09/250,839

(22) Filed: Feb. 16, 1999

Related U.S. Application Data

(63) Continuation-in-part of application No. 09/023,354, filed on Feb. 13, 1998, now abandoned.

(51) Int. Cl.[7] ............................................. C12N 15/63
(52) U.S. Cl. ..................... 435/455; 435/468; 435/472; 435/320.1; 435/235.1; 424/450; 424/486
(58) Field of Search .................. 424/480, 486; 514/44; 435/455, 320.1, 235.1, 472, 468

(56) References Cited

U.S. PATENT DOCUMENTS

| | | | |
|---|---|---|---|
| 3,828,980 A | 8/1974 | Creighton et al. ........... 222/137 |
| 3,956,044 A | 5/1976 | Bowen et al. ............. 156/73.2 |
| 4,044,126 A | 8/1977 | Cook et al. ................. 424/243 |
| 4,045,238 A | 8/1977 | Battista et al. .............. 106/122 |
| 4,222,671 A | 9/1980 | Gilmore ...................... 366/337 |
| 4,364,923 A | 12/1982 | Cook et al. .................... 424/46 |
| 4,414,209 A | 11/1983 | Cook et al. ................. 424/243 |
| 4,534,659 A | 8/1985 | Dourdeville et al. ........ 366/338 |
| 4,647,212 A | 3/1987 | Hankison ..................... 366/165 |
| 4,869,849 A | 9/1989 | Hirose et al. ............... 261/78.2 |
| 4,897,355 A | * 1/1990 | Eppstein et al. ............. 424/450 |
| 4,908,187 A | 3/1990 | Homquist et al. ............. 422/81 |
| 4,978,336 A | 12/1990 | Capozzi et al. ................ 604/82 |
| 4,979,942 A | 12/1990 | Wolf et al. .................... 604/83 |
| 5,088,499 A | * 2/1992 | Unger ....................... 424/9.51 |
| 5,116,315 A | 5/1992 | Capozzi et al. ................ 604/82 |
| 5,116,868 A | 5/1992 | Chen et al. .................. 514/546 |
| 5,218,088 A | 6/1993 | Gorenstein et al. ....... 536/25.34 |
| RE34,487 E | 12/1993 | Keller ......................... 222/137 |
| 5,277,914 A | * 1/1994 | Szoka ......................... 424/450 |
| D351,465 S | 10/1994 | Stringer et al. ............ D24/113 |
| D351,466 S | 10/1994 | Stringer et al. ............ D24/113 |
| 5,354,844 A | 10/1994 | Beug et al. .................. 530/345 |
| 5,505,704 A | 4/1996 | Pawelka et al. ............. 604/191 |

(List continued on next page.)

FOREIGN PATENT DOCUMENTS

| | | |
|---|---|---|
| WO | WO 95/25809 | 9/1995 |
| WO | WO 96/12006 | 4/1996 |
| WO | WO 96/36362 | 11/1996 |
| WO | WO 96/41606 | 12/1996 |

OTHER PUBLICATIONS

US 6,114,169, 9/2000, Bridenbaugh et al. (withdrawn)*
Verma et al. Nature 389: 239–242, especially p. 239, Sep. 1997.*
Anderson et al. Nature 392: 25–30, especially pp. 25 and 30, Apr. 1998.*

Primary Examiner—James Ketter
Assistant Examiner—Richard Schnizer
(74) Attorney, Agent, or Firm—Seed Intellectual Property Law Group PLLC

(57) ABSTRACT

The invention relates generally to methods and apparatuses that are adapted for the preparation of gene therapeutic compositions, as well as the compositions formed thereby. The invention also relates to methods adapted for making mixtures and condensate compositions. In the various embodiments, the present invention provides controlled and uniform mixing of gene therapy vectors and gene therapy vector vehicles for improved reproducibility, scaleability, stability, and pharmaceutical efficacy. Such compositions are suitable for use in mediation of disease.

28 Claims, 4 Drawing Sheets

U.S. PATENT DOCUMENTS

| | | | |
|---|---|---|---|
| 5,527,928 A | * 6/1996 | Nantz et al. | 554/105 |
| 5,534,328 A | 7/1996 | Ashmead et al. | 428/166 |
| 5,580,523 A | 12/1996 | Band | 422/50 |
| 5,595,712 A | 1/1997 | Harbster et al. | 422/129 |
| 5,595,897 A | 1/1997 | Midoux et al. | 435/172.3 |
| 5,635,383 A | 6/1997 | Wu et al. | 435/172.3 |
| D380,827 S | 7/1997 | Stringer et al. | D24/112 |
| 5,658,537 A | 8/1997 | Dugan | 422/191 |
| 5,690,763 A | 11/1997 | Ashmead et al. | 156/60 |
| 5,700,482 A | * 12/1997 | Frederiksen et al. | 424/450 |
| 5,714,166 A | * 2/1998 | Tomalia et al. | 424/486 |
| 5,766,899 A | * 6/1998 | Kuo et al. | 435/472 |

* cited by examiner

CONCURRENT FLOW MIXING METHODS AND APPARATUSES FOR THE PREPARATION OF GENE THERAPY VECTORS AND COMPOSITIONS PREPARED THEREBY

CROSS-REFERENCE TO RELATED APPLICATIONS

This application is a continuation-in-part of U.S. patent application Ser. No. 09/023,354, filed Feb. 13, 1998, abandoned.

TECHNICAL FIELD

The present invention relates generally to concurrent flow mixing methods and apparatuses that are adapted for preparation of gene therapeutics, as well as compositions prepared thereby. In the various embodiments, the present invention provides controlled and uniform mixing of gene therapy vectors and gene therapy vector vehicles for improved reproducibility, scaleability, stability, and pharmaceutical efficacy.

BACKGROUND

Ideally, techniques for nucleic acid delivery include one or more attributes, such as, for example: 1) efficient preparation of the nucleic acid delivery composition, including simplified operation, cost effectiveness, consistency, stability and uniformity; 2) efficient delivery and incorporation of the nucleic acid into the host cell; 3) avoidance of undesirable side effects such as cell toxicity, or the introduction of unwanted elements (e.g., additional viral genes); and 4) selective targeting of the nucleic acid to the desired host cell.

Various methods have been employed to introduce foreign genes into cells. Since DNA is a large and bulky molecule, it is no simple matter to introduce such molecules into cells, not only due to the size of the molecule but due to its chemical and charge-related characteristics. Therefore, many gene therapy methods endeavor to find a way to "package" the therapeutic DNA in such a manner that it may be transported across the membranes of the target cells. As those of skill in the art are well aware, this is not an easily-achieved goal. Moreover, most "packages" are comprised of components which interact with each other based on cooperative kinetics. Such kinetics are associated with bringing together components that each contain a variety of cooperative binding sites, thereby adding a level of complexity which when poorly controlled may lead to non-uniform compositions. Accordingly, to date, no methods are known to have been developed which control the cooperative kinetics involved in the manufacture of gene therapeutic compositions nor have methods been developed which allow for consistent, reproducible, and uniform (i.e., substantially homogenous) gene therapeutic compositions to be made.

One method of introducing therapeutic nucleic acids into host cells utilizes polycation/nucleic acid condensates. See, for example U.S. Pat. Nos. 5,166,320 and 5,635,383 as well as published International Patent App. Nos. WO 93/04701 and WO 94/06922. This methodology uses polycations to condense the nucleic acid into a compact structure so as to facilitate cellular uptake. However, such methodologies suffer from poorly controlled conditions for forming the condensates, thereby leading to aggregation or poorly condensed compositions.

Another current method of introducing foreign (or therapeutic) DNA into cells uses precipitation of DNA with calcium phosphate to form insoluble particles. Ideally, these particles become internalized in the host cells (via endocytosis) and induce expression of the new gene. Internalization of such particles, however, is independent of an endocytosis recognition site, so the internalization is non-specific and is thus not targetable to particular cells and organs. While generally applicable to in vitro applications, this process has more limited applicability in in vivo applications due to the insolubility of the DNA co-precipitate particles and the inability to control uptake and targeting specificity. Additionally, conditions necessary for internalization of DNA using the calcium phosphate method may be harsh and cause cell death.

An alternate method of introducing foreign genes into cells utilizes liposomes. Liposome-encapsulated DNA has been utilized both in vitro and in vivo. This technique, however, suffers from difficulties in controlling liposome size, which inherently affects uniform and controlled delivery to the target cell. There are also problems associated with keeping the liposome intact throughout the cell delivery process and difficulties associated with achieving specific targeting.

Other methods of delivering exogenous nucleic acids to cells have been proposed for use but suffer from a variety of limitations that make them impractical for gene therapy applications. For example, electroporation is impractical as the conditions required for gene delivery are harsh and lead to toxicity and cell death. Similarly, injection of naked DNA is unpredictable, especially with respect to targeting specificity, controlled uptake, and immunogenicity. Micro-injection of nucleic acids into cells is very labor intensive, because each cell must be individually manipulated, and thus it is not a practical alternative to bolus injections of DNA, although it avoids some of the problems associated with bolus injections. Thus, it is clear that none of the foregoing techniques provide a practical alternative for in vivo therapeutic applications.

The preparation of gene therapy vectors according to the methods described herein thus provides attractive means to improve upon known techniques and develop new gene transfer methods. The preparation and use of such vectors is not without its own unique limitations, however, as many have observed. Fortunately, the methods and apparatuses of the present invention overcome many of the difficulties experienced by others and enhance the efficacy of gene therapy for pharmaceutical commercialization.

Various methods of compacting nucleic acids to facilitate their entry into cells are described in the art and are useful to underscore the novel aspects of some embodiments of the present invention. The following examples are provided to illustrate some of those methods.

International Patent Publication WO 95/25809 describes nucleic acids that are compacted to facilitate their uptake by target cells of an organism. The publication further describes methods for compacting nucleic acids and therapeutic uses of the compacted DNA for delivery across the membrane of living cells.

International Patent Publication WO 96/41606 describes synthetic virus-like particles containing a plurality of peptides capable of condensing nucleic acid and condensed nucleic acid. The synthetic virus-like particle is self-assembling and may be designed to deliver nucleic acid to be incorporated into the chromosomal or extrachromosomal sequences of target cells. These particles are described as being useful for transfecting mammalian cells.

Other systems that have been developed to deliver nucleic acid molecules to mammalian cells include, emulsions (e.g., liposomes), nanoparticles, microparticles, and similar heterogeneous systems. However, these systems also suffer from lack of scaleable production methodologies that produce uniform, reproducible and highly efficacious compositions.

Of the aforementioned methods, compaction or condensation of the nucleic acids for delivery into the host cell offers great potential. For this technique to be fully exploited, however, methods and apparatuses for producing suitable nucleic acid complexes on a variety of scales, including for example, laboratory scale, commercial production scale, and individual patient bedside administration scale, are desirable. While a variety of mixing devices are available, some of which are exemplified below, they are not generally applicable to gene therapy vector and vehicle compositions and especially with regard to nucleic acid compaction or condensation methods.

For example, U.S. Pat. No. 4,908,187 describes a diluting and mixing device which is capable of diluting a first solution to produce a second solution which is mixed with an undiluted third solution to produce a unique series of combined solutions. Such a device is intended for use in obtaining kinetic analysis (e.g., chemical, biochemical or physical chemical) data on reactions in solution.

U.S. Pat. No. 4,979,942 describes a two-component syringe delivery system. In this system, two reactive fluids are delivered simultaneously and separately from a pair of syringes to a delivery site. The tubing exiting one syringe passes through a cannula exiting from the other syringe to deliver both fluids separately, but in a controlled volume and space to a delivery site. Alternatively, the fluids can mix within the cannula; purportedly, its configuration prevents clogging at the delivery site.

U.S. Pat. Nos. 4,978,336 and 5,116,315 describe a biological syringe system for delivering a first and second fluid in a mixed composition comprising a manifold and a discharge assembly. The discharge assembly has a mixing space and further comprises a mixing mechanism to thoroughly mix the first and second fluids and to immediately thereafter atomize the thoroughly mixed fluids in a spray discharge from the discharge assembly. This apparatus is described as being particularly useful for applying a chemically formed tissue adhesive and protective covering.

U.S. Pat. No. 5,505,704 describes a hand-held liquid medication injector having dual, bidirectional dosage metering mechanisms for permitting a variable dosage amount for each cartridge of liquid medication. The medication injector has an injection mechanism independent of the metering mechanism that loads and injects the liquid medication.

The apparatuses described above are similar to each other in that they are used to mix two solutions. There is no indication, however, that these apparatuses would be useful or suitable for providing uniform gene therapy vector mixtures or uniform condensate particles, particularly where the control of such uniformity and/or condensate particle size is critical. Accordingly, the need exists for methods and apparatuses to make gene therapeutic vector and vehicle mixtures of uniform quality, of a defined particle size in a convenient manner (e.g., when using a condensing agent), and ideally in a manner that is adaptable enough to be amenable to scale-up without sacrificing the quality of the compositions produced.

SUMMARY OF THE INVENTION

The invention relates to methods and apparatuses, including "concurrent flow mixing" methods and apparatuses, for providing gene therapy vector and vehicle compositions (e.g., mixtures, complexes, and condensates) of precisely controlled uniformity (i.e., substantially homogenous) as well precisely controlled particle size for condensate complexes. These methods and apparatuses simultaneously control the rate of introduction of reactants, mixing of the reactants and removal of the resulting mixture. Accordingly, the methods and apparatuses of the present invention are capable of regulating the cooperative kinetics of the formation of various gene therapy vector and vehicle mixtures, complexes, and condensates (collectively, compositions).

In one embodiment, methods are provided for the preparation of gene therapy compositions, comprising concurrently introducing at least a first molecular entity-containing solution and a second molecular entity-containing solution, each in a controlled and independent manner, into at least a first flow-through mixer such that the two solutions contact, mix, and form a uniform mixture, such that said uniform mixture exits from the flow-through mixer at a controlled rate, and wherein said first and second molecular entity-containing solutions collectively comprise at least one gene therapy vector and at least one gene therapy vehicle.

In the various embodiments, described herein, the mixer may be a static mixer or may be a dynamic mixer.

In another aspect, the invention provides a method of preparing a gene therapy composition, comprising DNA-:condensing agent condensation complex of a predetermined size comprising the steps of: a) providing i) a DNA-containing solution, ii) a condensing agent-containing solution, and iii) a flow-through mixer; and b) concurrently introducing said DNA-containing solution and said condensing agent-containing solution, each in a controlled and independent manner, into said mixer such that the two solutions contact, mix, and form a mixed solution containing a DNA:condensing agent condensation complex of predetermined size thereby, and such that said condensation complex exits from the flow-through mixer at a controlled rate such that further reaction of the desired DNA:condensing agent condensation complex with additional DNA- and/or condensing agent-containing solution is minimized or avoided.

The methods and apparatuses described herein include those wherein the condensing agent comprises a polycationic molecule. Polycationic molecules useful in the methods and apparatuses of the invention are exemplified by molecules including, for example, polycationic peptides or polypeptides; polycationic proteins; polycationic polyamino acids; polycationic carbohydrates; polycationic synthetic polymers; polycationic small synthetic organic amines; inorganic multivalent cations; cationic lipids; and synthetic viral particles.

The methods and apparatuses described herein are suitable for providing molecular entity condensation complexes of uniform particle size, including, for example, complexes having a particle size of about 2000 nm or smaller, alternatively of about 1000 nm or smaller, alternatively of about 500 nm or smaller, alternatively of about 200 nm or smaller, alternatively of about 100 nm or smaller, or alternatively of about 50 nm or smaller. The methods described herein are also suitable for providing condensation complexes in a range of particle sizes, including for example, from about 30 to about 2000 nm, alternatively from about 30 to about 200 nm, or alternatively of from about 30 to about 100 nm.

In another embodiment, the invention relates to apparatuses for preparing gene therapy compositions comprising: a) a first molecular entity-containing solution dispenser; b)

a second molecular entity-containing solution dispenser; c) a mixer attached to a solution removal outlet, wherein the first molecular entity-containing solution dispenser and the second molecular entity-containing solution dispenser are each independently connected to the mixer; and d) a solution flow controller that independently controls the rate of introduction of the first molecular entity-containing solution and the second molecular entity-containing solution into the mixer, and the rate of flow of the resulting mixed solution through the mixer and out to the solution removal outlet, and wherein said first and second molecular entity-containing solutions collectively comprise at least one gene therapy vector and at least one gene therapy vehicle. Such a method is referred to herein as concurrent flow mixing (CFM).

In further embodiments, the invention relates to apparatuses for preparing gene therapy compositions, comprising: a) a first molecular entity-containing solution introduction means; b) a second molecular entity-containing solution introduction means; c) a mixing means attached to a solution removal means, wherein the first molecular entity-containing solution introduction means and the second molecular entity-containing solution means are each independently connected to the mixing means; and d) a solution flow controller that independently controls the rate of introduction of the first molecular entity-containing solution and the second molecular entity-containing solution into the mixing means, and the rate of flow of the resulting mixed solution through the mixing means and out to the solution removal means.

In other embodiments, the invention provides an apparatus for preparing a DNA:condensing agent condensation complex of a predetermined size comprising: a) a DNA-containing solution dispenser; b) a condensing agent-containing solution dispenser; c) a mixer attached to a solution removal outlet, wherein the DNA-containing solution dispenser and the condensing agent-containing solution dispenser are each independently connected to the mixer; and d) a solution flow controller that independently controls the rate of introduction of the DNA-containing solution and the condensing agent-containing solution into the mixer, the size of the DNA:condensing agent condensation complex formed thereby, and the rate of flow of the resulting mixed solution through the mixer and out to the solution removal outlet.

In even further embodiments, the invention provides an apparatus, comprising: a) a DNA-containing solution introduction means; b) a condensing agent-containing solution introduction means, c) a mixing means attached to a solution removal means, wherein the DNA-containing solution introduction means and the condensing agent-containing solution means are each independently connected to the mixing means, and d) a solution flow controller that independently controls the rate of introduction of the DNA-containing solution and the condensing agent-containing solution into the mixing means, the size of the DNA:condensing agent condensation complex formed thereby, and the rate of flow of the resulting mixed solution through the mixing means and out to the solution removal means.

In addition, the methods and apparatuses of the present invention may readily be modified to accommodate "stacking" or "piggybacking" of components (e.g., dispensers, flow controllers, etc.). For example, FIG. 2 illustrates another embodiment of such an apparatus.

One example of a rationale for "piggybacking" would be to allow multiple reactant solutions to be admixed. Another example would be to allow multiple components to be connected to a single flow controller. Other rearrangements, interconnections and modifications are contemplated and are within the scope of this invention, as well as within the purview of the skilled artisan to accomplish, following the teachings of this application.

Thus, the present invention also discloses methods and apparatuses that accommodate "branched" configurations, whereby multiple components (e.g., dispensers, mixers, flow controllers, etc.) may be used in a single system. For example, one nucleic acid may be admixed with a first condensing agent, and a second nucleic acid may be admixed with a second condensing agent, and then the two complexes may thereafter be admixed to form a condensation complex comprising two different nucleic acids, two different condensing agents, or combinations of same. In another example, a nucleic acid (e.g., DNA) may be admixed with a first condensing agent, ligand, other reagent, or some combination of the same to form a first condensation complex; subsequently, that first condensation complex may be admixed with a second condensing agent, ligand, other reagent, or some combination of the same to form a second condensation complex. A wide variety of condensation complexes—particularly those having increased stability and/or particle size uniformity—may be made using the methods and apparatuses of the present invention and are thus contemplated within the scope of the present invention, as well.

Other embodiments of the invention are disclosed herein and include methods and apparatuses wherein the first molecular entity is a nucleic acid and the second molecular entity is a condensing agent. In various disclosed embodiments, the nucleic acid is a therapeutic nucleic acid; in other embodiments, the nucleic acid or therapeutic nucleic acid is DNA.

In further embodiments, compositions produced by the methods and apparatuses, described herein, are provided.

DETAILED DESCRIPTION

Figure 1:
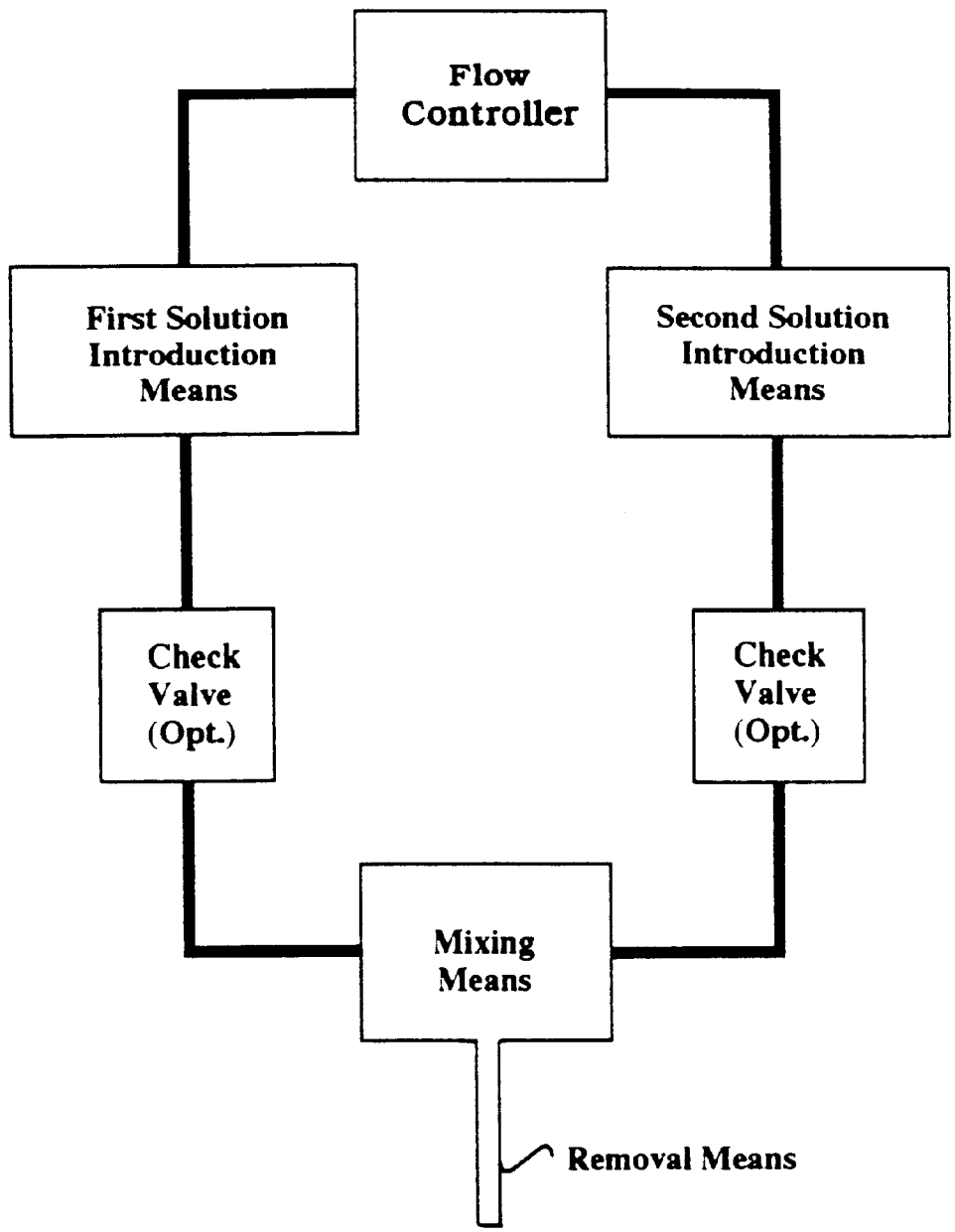
FIG. 1 is a general schematic of an embodiment of an apparatus according to the invention.
Figure 2:
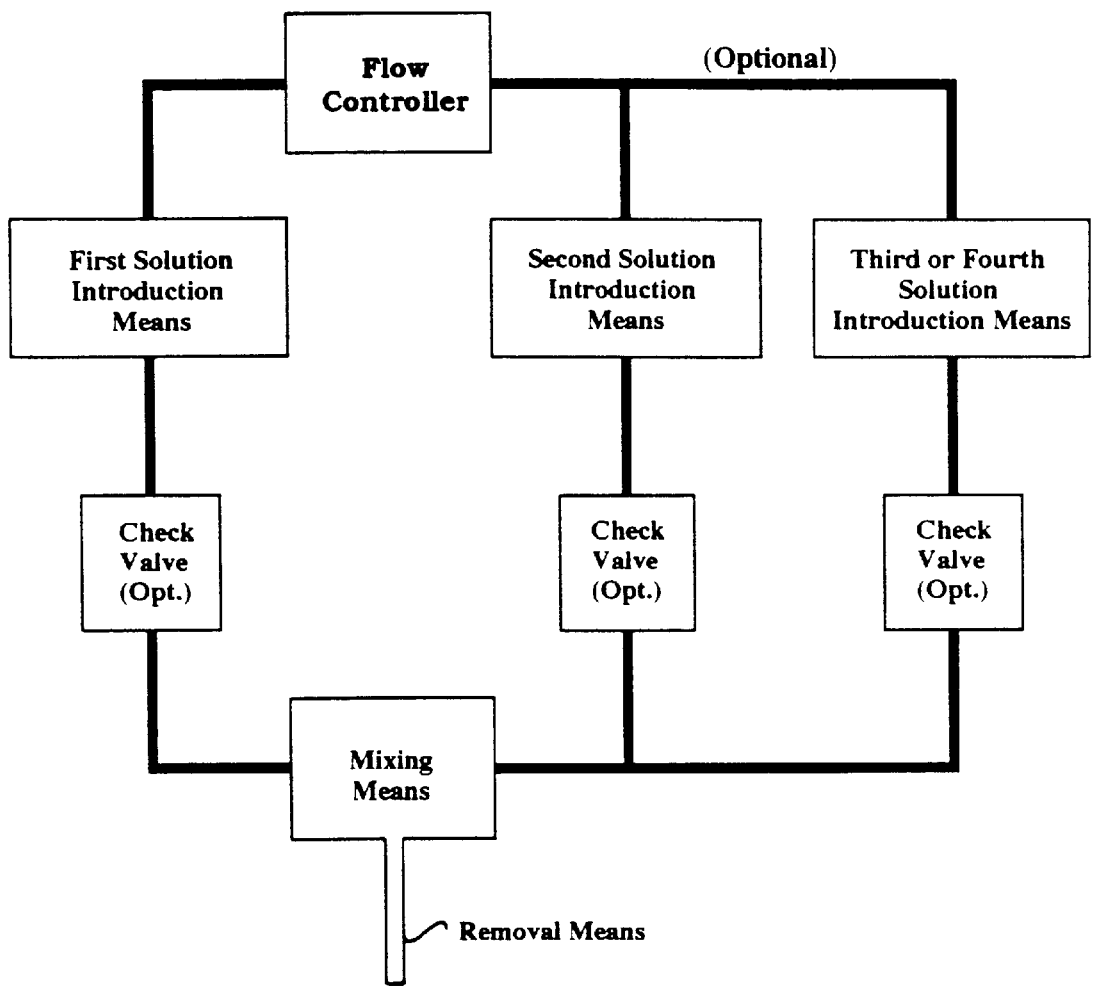
FIG. 2 is a general schematic of another embodiment of an apparatus according to the invention.

In order that the invention described herein may be more fully understood, the following detailed description is set forth.

The methods and apparatuses described herein produce gene therapy vector and vehicle mixtures, complexes, and condensates of a uniform quality and consistency. Uniform quality, consistency and specific particle size (for condensates) are critical for achieving consistent and reliable efficacious nucleic acid delivery via transfection into host cells and are also critical for cell, tissue or organ target specificity; that is, specific cell types may be transfected by particles of a certain size range while other cell types may not. Accordingly, when using condensing formulations particle size can be readily regulated by controlling the mixing ratio. Both size and mixture uniformity are dependent upon maintaining the proper mixing ratio, flow rate and mixing rate of the reaction between the gene therapy vectors and the vehicles. Since other reactants or molecular entities (e.g., solution components and matrix formulations) may also be included, the flow rate, mixing rate and ratio of these other, optional entities must also be regulated. This may be accomplished by control of important reaction parameters as described below.

Although many of the following parameters are described by way of example in a DNA (gene therapy vector) :condensing agent (vehicle) context, the principles therein are similarly applicable to all molecular entities that may be subject to mixture formulation or complexation reactions with gene therapy vectors and thus the methods and apparatuses described herein are likewise suitable for such formulations and reactions.

Definitions

Prior to setting forth further details of the present invention, it may be helpful to an understanding thereof to set forth definitions of certain terms that will be used hereinafter.

"Uniform mixture" as used herein, refers to a substantially homogeneous mixture, such that the components are thoroughly mixed. Homogeneity, is used with respect to the amount added. For example, if the methods of the present invention are used to mix an adenovirus with a targeting ligand, then homogenous would refer to the fact that the resulting product has an approximately equal number of targeted adenovirus particles per preparation. Furthermore, when preparing heterogeneous systems such as emulsions, the term homogenous is meant to connote that each of the particles of the emulsion are of approximately uniform consistency and contain approximately the same amount of therapeutic nucleic acid. Accordingly, the terms uniform and homogenous further describe the product of the inventive methods as a whole or a comparison of the individual particles created within a singular preparation.

"Nucleic acid binding domain" (NABD) refers to a molecule, usually a protein, or peptide (but may also be a polycation) that binds nucleic acids, such as DNA or RNA. An NABD may bind to single or double strands of RNA or DNA or mixed RNA/DNA hybrids. The nucleic acid binding domain may bind to a specific sequence or bind irrespective of the sequence.

As used herein, "operative linkage" or operative association of two nucleotide sequences refers to the functional relationship between such sequences. Nucleotide sequences include, but are not limited to, DNA encoding a product, DNA encoding a signal sequence, promoters, enhancers, transcriptional and translational stop sites, and polyadenylation signals. For example, operative linkage of DNA encoding a therapeutic product to a promoter refers to the physical and functional relationship between the DNA and the promoter such that transcription of the DNA is initiated from the promoter by an RNA polymerase that specifically recognizes, binds to, and transcribes the DNA.

As used herein, "receptor-binding internalized ligand" or "ligand" refers to any peptide, polypeptide, protein or non-protein, such as a peptidomimetic, that is capable of binding to a cell-surface molecule and internalization. Within the context of this invention, the receptor-binding internalized ligand is conjugated to a gene therapy vector or gene therapy vector vehicle, either as a fusion protein or through chemical conjugation, and is used to deliver a therapeutic encoding agent to a cell. In one aspect, the ligand is directly conjugated to the vehicle (e.g., a nucleic acid binding domain, including a polycation), which may be further complexed with other vehicles and/or a vector. Such ligands include growth factors, cytokines, antibodies, hormones, and the like.

"Amino acids," as the term is used herein, are identified according to their well-known three letter or one letter abbreviations. The term "amino acids" also includes modified or unusual amino acids such as those exemplified in 37 C.F.R. §1.822 (with delineated abbreviations), herein incorporated by reference.

As used herein, the terms "oligonucleotide" or "nucleic acid" refer to any DNA or RNA, or a combination thereof, and includes, but is not limited to, DNA encoding a therapeutic protein, a cytotoxic protein, a prodrug, a ribozyme, or antisense, the complement of these DNAs, an antisense nucleic acid, and other such molecules. Reference to nucleic acids includes duplex DNA, single-stranded DNA, RNA in any form, including triplex, duplex or single-stranded RNA, anti-sense RNA, ribozymes, deoxyribozymes, polynucleotides, oligonucleotides, single nucleotides, chimeras, and derivatives thereof. Nucleic acids may be composed of the well-known deoxyribonucleotides and ribonucleotides (i.e., the bases adenosine, cytosine, guanine, thymidine, and uridine). As well, various other nucleotide derivatives, non-phosphate backbones or phosphate-derived backbones may be used. For example, because normal phosphodiester oligonucleotides (referred to as PO oligonucleotides) are sensitive to DNA- and RNA-specific nucleases, oligonucleotides resistant to cleavage, such as those in which the phosphate group has been altered to a phosphotriester, methylphosphonate, or phosphorothioate may be used (see U.S. Pat. No. 5,218,088). Furthermore, nucleic acids may comprise modified nucleotide bases such as those exemplified in 37 C.F.R. §1.822 (with delineated abbreviations), hereby incorporated by reference.

As used herein, a "gene therapy vector" or "vector" refers to an agent comprising a therapeutic nucleic acid molecule capable of being directed into a mammalian cell, wherein the nucleic acid, once introduced, encodes a therapeutic product (e.g., naked nucleic acid, viral vectors, bacteriophage, etc.). However, when the context is clear, the term "vector" can also relate to a plasmid.

As used herein, a "gene therapy vector vehicle", "gene therapy vehicle", or "vehicle" refers to an agent suitable for facilitating cellular uptake of the gene therapy vector. Accordingly, this term encompasses pharmaceutical buffers, bulking agents, and emulsifiers, but more preferably comprises condensing agents, targeting agents (ligands), and/or matrix formulation agents. In some embodiments the invention may include lipids, such that the vector, upon mixing, is emulsified therein. In the various embodiments, three major categories of vehicles are utilized and include: 1) those that bind to, neutralize the charge of, compact, reduce size of, incorporate, encapsulate, target, protect, facilitate stability, facilitate storage, or facilitate delivery of a gene therapy vector; 2) a group of matrix forming materials to create three dimensional structures to facilitate cell in-growth, and 3) pharmaceutical carriers. However, as one of ordinary skill in the art would readily recognize, these categories are not mutually exclusive as a variety of overlap exists.

As used herein, a "therapeutic nucleic acid" describes any nucleic acid molecule used in the context of the invention that effects an alteration or a treatment, generally by modifying gene transcription or translation. It includes, but is not limited to, the following types of nucleic acids: nucleic acids encoding a protein, antisense RNA, DNA intended to form triplex molecules, protein binding nucleic acids, ribozymes, deoxyribozymes, and small nucleotide molecules. A therapeutic nucleic acid may be used to effect genetic therapy by serving as a replacement or enhancement for a defective gene or to compensate for lack of a particular gene product, by encoding a therapeutic product (e.g., factor VIII, PDGF, PTH, growth factors, etc.) by encoding a prodrug (e.g., HSVtk), or by encoding a cytotoxic molecule (e.g., saporin). A therapeutic nucleic acid may encode all or a portion of a translation product, and may function by recombining with DNA already present in a cell, thereby replacing a defective portion of a gene. It may also encode a portion of a protein and exert its effect by virtue of co-suppression of a gene product.

As used herein, "stable" refers to the ability of the nucleic acid containing composition to maintain integrity with regard to thermolability and well as typical storage conditions for pharmaceutical compositions. Accordingly, greater stability of a concurrent flow mixed compositions would be in comparison to a similar composition, produced by non-concurrent flow or other standard methodologies.

As used herein, the term "molecular entity-containing" refers to a solution or compound containing multiple molecules, and does not necessitate that the solution or compound contain only a singular "molecule". Accordingly, as used herein, when referring to a solution, the term is meant to indicate that the solution contains at least one component which will comprise the final gene therapeutic composition. Exemplary molecular entity-containing solutions in this regard are solutions containing a condensing agent, as solution containing a viral vector, and a solution containing naked nucleic acid.

As used herein, the term "solution" refers to a fluid or liquid, containing a component of the gene therapy vector or gene therapy vehicle composition. Accordingly, the term solution is used broadly to encompass such fluids as colloidal dispersion, suspensions, emulsions, gels, etc.

Concurrent Flow Mixing Methodologies

The present invention describes methodologies and apparatuses for concurrent flow mixing ("CFM") of gene therapy vectors and associated vehicles, thereby providing a convenient, scaleable, and reproducible preparation of gene therapy compositions. Generally, the method comprises providing a first molecular entity-containing solution, a second molecular entity-containing solution and a flow through mixer and simultaneously introducing the first and second solutions in a controlled and independent manner into the mixer. In the various embodiments, the first molecular entity-containing solution, comprises a gene therapy vector (e.g., a therapeutic nucleic acid molecule as a naked nucleic acid molecule, in a virus, within a bacteriophage, etc.). In the various embodiments, the second molecular entity-containing solution, comprises a gene therapy vector vehicle (e.g., a targeting ligand, a matrix formulation, a condensing agent, pharmaceutical carrier, etc.). In other embodiments, any or all of the solutions may comprise a non-aqueous medium, wherein components may be dissolved (e.g., dimethylsufloxide, etc.).

In further aspects of the present invention, multiple molecular entity-containing solutions are provided in two or more reservoirs. Accordingly, in one embodiment, three reservoirs may be utilized such that the mixing of three molecular entity-containing solutions can take place. When utilizing more than two solutions, it may be of use to delay introduction of one or more solutions until mixing of the first components are substantially complete or in some embodiments to control uniformity it may be advantageous to link several flow-through mixtures such that upon completion of mixing in one mixer additional components may be added at a second mixer. Such multiple mixer configurations are useful in preventing non-uniform composition formation, if a third or more components cannot be added to the first two prior to their complete mixing. Alternatively, it may be advantageous to simultaneously mix all components. In one embodiment, the first molecular entity comprises a nucleic acid molecule and the second molecular entity comprises a condensing agent, upon controlled mixing the condensation complex size and/or mixture uniformity can be strictly and reproducibly controlled. In a further embodiment, either concurrently with condensation, but preferably following condensation a third molecular entity-containing solution is added to the mixture. The third molecular-entity containing solution, may comprise a variety of other vehicles, including matrix formulations (e.g., collagens, hydrogels, cellulose, carboxymethylcellulose, as well as other natural and synthetic matrix compositions).

In further embodiments, the methods and apparatuses of the present invention can be used to produce solutions, colloidal dispersions, suspensions, emulsions, and pastes. In one aspect, non-aqueous medium may be utilized such that biological (e.g., nucleic acids, viruses, etc.) and non-biologics, such as synthetics may be dissolved within the same solution. Further, the methods and apparatuses of the present invention can used to adjust pH, solvent composition, or temperature of any of the solutions, such that the consistency, solubility, or viscosity of the product (e.g., solution, paste, etc.) may be regulated. Accordingly, the methods and apparatuses described herein, can be utilized to manufacture monolithic micro- and nano-particles of uniform size and consistency as well as providing the ability to control emulsion formation and consistency. The particles and compositions that can be reproducibly produced by the present invention are numerous, exemplary patents and patent applications that describe these various formulations are incorporated herein by reference and include, U.S. Pat. Nos. 5,827,703, 5,705,385, 5,531,925, 5,512,295, 5,283,185, and 5,279,833; and published International Patent App. Nos. WO 95/25809 and WO 96/20698.

In another related embodiment, the first molecular entity-containing solution may comprise a viral vector and the second molecular entity-containing solution may comprise a targeting ligand, such that upon controlled concurrent mixing the viral vector is complexed with the targeting ligand (e.g., an anti-fiber antibody or Fab conjugated to a ligand for a cellular receptor). See for example, U.S. patent application Ser. No. 08/761,242 which issued Feb. 16, 1999 and which is incorporated herein by reference. Accordingly, one of ordinary skill in the art, upon referencing the present specification, could readily utilize multiple reservoirs for concurrently mixing multiple gene therapy vectors simultaneously, thereby providing a composition comprising more than one therapeutic DNA. In the same regard, multiple vehicles could be distributed in multiple reservoirs, thereby allowing uniform mixing of a variety of combinations of gene therapy vectors and vector vehicles.

The advantages of CFM within the context of gene therapy, are many fold. For example, no other mixing format allows for convenient, reliable, reproducible, and scaleable methodologies. These characteristics of CFM, as adapted to gene therapy vector and vehicle compositions, are essential for obtaining reliable clinical data with respect to safety and efficacy, and ultimately commercialization. Moreover, when a condensed nucleic acid composition is desired, no other mixing format allows for reproducible and strict control over particle size. Importantly, particle size, itself, may play a role in transfection efficiency. Further, the particle size of the condensate will necessarily vary depending on the application. For example, for systemic delivery of a gene therapeutic, small particles will be more efficacious, while when delivering from a more structured vehicle such as a matrix, larger particle size may be desirable. Also, when non-condensed gene therapy vector and vehicle compositions are desired, the uniformity of mixing provided by the present invention will enhance efficacy as well as decrease toxicity, by providing a continuous dosing of the gene therapy vector and vehicle composition. In addition, particles formed by the present invention have increased stability.

One particularly advantageous feature of the present invention, is the ability to overcome the difficulties associated with the cooperative nature of the formation of a gene therapy vector and targeting agent complex or a gene therapy vector and vehicle complex. Simple cooperative kinetics of the binding of two components are described by the equation:

$$v = nK[L]^m / 1 + K[L]^m$$

In the above equation, K is the equilibrium constant, L is the concentration of one of the interacting components, while n, represents the number of potential binding sites between the molecules, and m, represents the degree of interactivity between the binding sites. In addition, a variety of other equations are known in the art which describe more complex cooperative kinetic mechanisms, such as the formation of the quaternary structure of a protein based on helical polymerization. See for example, Oosawa and Kasai, *J. Mol. Biol.* 4:12, 1962.

As one of skill in the art readily understands, the essence of cooperativity is that, at least to a point, the further the reaction proceeds, the rate of reaction increases, that is, the reaction is more likely to occur with an existing reaction intermediate rather than one the initial reaction components. When a cooperative process is not controlled, the interaction of two molecules with multiple binding sites would lead to the formation of a small population of higher order complexes (i.e. aggregates) as opposed to a large population of lower order complexes (i.e. small particles). A well documented form of this cooperative phenomenon occurs when nucleic acids condense. See, for example, Bloomfield, *Biopolymers* 44(3):269–82, 1997. Accordingly, given these cooperative phenomena, it is critical to be able to control the introduction rates for components, in order to avoid system saturation and/or sub-optimal (e.g., non-uniform or aggregate complex formation) gene therapy vector formulations.

Gene Therapy Vectors

Any number of known gene therapy vectors may be utilized within the context of the present invention. Within the context of the present invention a "gene therapy vector" refers to an agent comprising a therapeutic nucleic acid molecule capable of being directed into a mammalian cell, wherein the nucleic acid, once introduced, encodes a therapeutic product. Accordingly, such vectors include, for example, naked DNA in operative associate with a promoter such that expression is achieved upon introduction to a cell, micro- or nano-particles containing the therapeutic nucleic acid molecule, adenoviral vectors containing the therapeutic nucleic acid molecule, retroviral vectors containing the therapeutic nucleic acid molecule, and bacteriophage containing the therapeutic nucleic acid molecule. In addition, such vectors may be prepared as targeted forms. For example, naked DNA may be complexed with a nucleic acid binding domain which itself is conjugated to a cell receptor binding-internalizing ligand (see, e.g., published International App. No. WO 96/36362), adenoviral vectors may be "re-targeted" by complexing the adenovirus with an anti-surface protein antibody or fragment thereof conjugated or genetically fused to an internalizing ligand (see, U.S. Pat. No. 5,871,727 and published International App. No. WO 98/40508, retroviral vectors may also be modified to alter their natural tropism and target cells (see, e.g., published International App. No. WO 98/51808) and bacteriophage may be targeted via expression or attachment of an internalizing ligand on their surface (see, PCT/US98/17950).

Nucleic acids, such as DNA, and targeted nucleic acid molecules that are contemplated for use in the methods and apparatuses of the invention, include any DNA-containing molecule or DNA derivative (recombinant or otherwise) that effects a cellular function upon internalization in a host cell. A nearly-infinite variety of nucleic acids may be utilized in complexes formed using the methods and apparatuses of the present invention; see, e.g., the disclosures of published International App. No. WO 96/36362. The DNA may be in the form of genomic DNA, or plasmid DNA, either linear or circular, or may be in the form of a DNA fragment, such as an oligonucleotide.

In addition, other methods of vectors and methods of targeting are known in the art, for example, published International App. No. WO 95/26412, U.S. Pat. No. 5,543,328, and Krasnykh, et al. (*J. Virol.* 70: 6839–46 (1996)), the disclosures of which are incorporated by reference herein, describe modifications that may be made to the adenovirus fiber protein. Such modifications are useful in altering the targeting mechanism and specificity of adenovirus and could readily be utilized to target different receptors and different cells. Similarly, modified penton base polypeptides such as those described in Wickham, et al. (*J. Virol.* 70: 6831–8 (1996)) may have therapeutic utility when modified to comprise an internalizing ligand. Furthermore, methods of preparing anti-viral antibodies—and the antibodies so prepared—are available and are useful according to the within-disclosed methods, as well. For example, U.S. Pat. No. 5,521,291 (the disclosures of which are incorporated by reference herein) describes a method of preparing a chimeric adenovirus having a heterologous epitope exposed in the exterior domain of its hexon protein.

With regard to bacteriophage, preferred gene therapy vectors for use in the present invention include filamentous phage particles having one or more preselected ligands on the viral particle surface, irrespective of the manner in which the ligands are attached. Therefore, whether the means of attachment of a ligand is covalent or via a fusion protein, the targeted phage vectors of the present invention are able to deliver therapeutic nucleotide sequences to target cells. Various preferred methods and modifications to ligands that may facilitate the linkage between the ligand and the phage protein are disclosed in published International App. No. WO 96/36362.

Gene Therapy Vector Vehicles

When formulating a gene therapeutic vector, the vehicle chosen depends on the type of desired application. In the various embodiments, three major categories of vehicles are utilized and include: 1) those that bind to, neutralize the charge of, compact, reduce size of, incorporate, encapsulate, target, protect, facilitate stability, facilitate storage, or facilitate delivery of a gene therapy vector; 2) a group of matrix forming materials to create three dimensional structures to facilitate cell in-growth, and 3) pharmaceutical carriers. For example, for systemic delivery, a condensing agent and/or an additional pharmaceutical carrier would necessarily be the vehicle of choice (e.g., emulsifiers, buffers, bulking agents, etc.), whereas for topical applications gels, ointments, pastes, and cream formulations may be useful.

For other internal uses an implant or injectible is preferred and may comprise a hydrogel, fibrillar collagen, or other matrix formulations may be optimal in its ability to retain the gene therapy vector at the desired location, while promoting cell ingrowth and DNA uptake by repair cells. The present invention provides the ability to uniformly mix a gene therapeutic vector and the vehicle of choice under strictly controlled conditions, such that the mixture of the vector and vehicle are independently regulated.

In one embodiment of the present invention condensing agents are the preferred vehicles used for naked DNA vectors. Such condensing can also be conjugated to internalizing ligands, as described above.

Matrix Formulations

Matrix formulations, within the context of the present invention, are biocompatible. Bio-compatible matrices capable of being used in the present invention include, but are not limited to, biodegradable or non-biodegradable materials which can be formulated to contain a gene therapy vector(s). They may function as controlled delivery devices for the gene vector(s), in some cases they also act as scaffolds that support cell attachment and growth. Depending upon their therapeutic application, they may exist as a porous or non-porous 3-D structure for an implant, a gel, ointment, cream, or paste for topical use, or monolithic nanoparticles, microparticles, gel, emulsion, or microcapsules for injection/internal use.

Matrices may be derived from synthetic polymers or naturally occurring polymers including proteins such as polymers of lactic acid and glycolic (e.g., PLGA), chitosan, collagen, cellulose, or cellulose derivative (e.g., carboxymethylcellulose, methyl cellulose, etc.), other extracellular matrix proteins, or other structural macromolecules.

In one aspect, compositions are prepared by the methods and apparatuses of the invention, in which the DNA encoding the therapeutic agent of interest is associated with or impregnated within a matrix to form a gene activated matrix. The matrix compositions function (i) to facilitate ingrowth of repair cells; and (ii) to harbor a gene therapy vector. In addition, matrices can be designed to allow for controlled release of the gene vector to the ingrown/infiltrated cells and/or those that are surrounding the matrix.

The type of matrix formulations that may be used in the methods, apparatuses, and compositions of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from both natural or synthetic materials. The matrices may be non-biodegradable in instances where it is desirable to leave permanent structures in the body; or biodegradable where the expression of the therapeutic protein is required only for a short duration of time. The matrices may take the form of an implant (e.g., porous and non-porous 3-D structure devices), an externally applicable dosage form (e.g., suture, tube, tefla pads, band-aids, bandages, pads, lyophilized components, gels, patches, pastes, lacquer, powders, etc.), or an injectable (non-aqueous solution, gel, colloidal dispersion, suspension, emulsion, etc.).

The choice of matrix material will differ according to the particular circumstances and the site to be treated. Matrices such as those described in U.S. Pat. Nos. 5,270,300 and 5,763,416, as well as published International App. No. WO 97/38729, which are incorporated herein by reference, may be employed. Physical and chemical characteristics, such as, e.g., biocompatibility, biodegradability, strength, rigidity, interface properties and even cosmetic appearance may be considered in choosing a matrix, as is well known to those of skill in the art. In various embodiments, appropriate matrices will both deliver the DNA molecule and also act as an in situ scaffolding through which mammalian repair cells may migrate.

Where the matrices are to be maintained for extended periods of time, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. The bioceramics may be altered in composition, such as in calcium-aluminate-phosphate; and they may be processed to modify particular physical and chemical characteristics, such as pore size, particle size, particle shape, and biodegradability. Polymeric matrices may also be employed, including acrylic ester polymers and lactic acid polymers, as disclosed in U.S. Pat. Nos. 4,521,909, and 4,563,489, respectively, each incorporated herein by reference. Particular examples of useful polymers are those of orthoesters, anhydrides, propylene-cofumarates, or a polymer of one or more γ-hydroxy carboxylic acid monomers, e.g., γ-hydroxy auric acid (glycolic acid) and/or γ-hydroxy propionic acid (lactic acid).

The available chemical groups of the absorptive material, such as hydroxyl apatite, may be readily manipulated to control its affinity for nucleic acids, as is known to those of skill in the art.

In preferred embodiments, it is contemplated that a biodegradable matrix will likely be most useful. A biodegradable matrix is generally defined as one that is capable of being reabsorbed into the body. Potential biodegradable matrices for use in connection with the compositions, devices and methods of this invention include, for example, biodegradable and chemically defined calcium sulfate, tricalciumphosphate, hydroxyapatite, polylactic acid, polyanhidrides, matrices of purified proteins, and semi-purified extracellular matrix compositions.

Other biocompatible biodegradable polymers that may be used are well known in the art and include, by way of example and not limitation, polyesters such as polyglycolides, polylactides and polylactic polyglycolic acid copolymers ("PLGA") (Langer and Folkman, 1976, Nature 263:797–800); polyethers such as polycaprolactone ("PCL"); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers.

It is to be understood that virtually any polymer that is now known or that will be later developed suitable for the sustained or controlled release of nucleic acids may be employed in the present invention.

In preferred embodiments, the biocompatible biodegradable polymer is a copolymer of glycolic acid and lactic acid ("PLGA") having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

The length of the period of continuous sustained or controlled release of nucleic acids from the matrix according to the invention will depend in large part on the MW of the polymer and the composition ratio of lactic acid/glycolic acid. Generally, a higher ratio of lactic acid/glycolic acid, such as for example 75/25, will provide for a longer period of controlled or sustained release of the nucleic acids, whereas a lower ratio of lactic acid/glycolic acid will provide for more rapid release of the nucleic acids. Preferably, the lactic acid/glycolic acid ratio is 50/50.

The length of period of sustained or controlled release is also dependent on the MW of the polymer. Generally, a higher MW polymer will provide for a longer period of controlled or sustained release. In the case of preparing, for example, matrices providing controlled or sustained release for about three months, when the composition ratio of lactic acid/glycolic acid is 100/0, the preferable average MW of polymer ranges from about 7,000 to 25,000; when 90/10, from about 6,000 to 30,000; and when 80/20, from about 12,000 to 30,000.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., J. Surg. Res. 47:74–80, 1989. SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use.

Another particular example of a suitable material is fibrous collagen, which may be lyophilized following extraction and partial purification from tissue and then sterilized. Matrices may also be prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527, each incorporated herein by reference.

In addition, matrices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which repair cells may migrate. Collagen matrix, such as those disclosed in Bell, U.S. Pat. No. 4,485,097, may also be used as a matrix material.

The various collagenous materials may also be in the form of mineralized collagen. For example, the fibrous collagen implant material termed UltraFiber™, as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils. Such a formulation may be employed in the context of delivering a nucleic acid segment to a bone tissue site.

At least 20 different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from rat tail tendon may be purchased from, e.g., Collagen Corporation. Any form of recombinant collagen may also be employed, as may be obtained from a collagen-expressing recombinant host cell, including bacterial yeast, mammalian, and insect cells. When using collagen as a matrix material it may be advantageous to remove what is referred to as the "telopeptide" which is located at the end of the collagen molecule and known to induce an inflammatory response.

The collagen used in the invention may, if desired be supplemented with additional minerals, such as calcium, e.g., in the form of calcium phosphate. Both native and recombinant type collagen may be supplemented by admixing, absorbing, or otherwise associating with, additional minerals in this manner. For example, U.S. Pat. No. 5,231,169, incorporated herein by reference, describes the preparation of mineralized collagen through the formation of calcium phosphate mineral under mild agitation in situ in the presence of dispersed collagen fibrils. While many collagen formulations are useful, in some aspects recombinant type II collagen or mineralized type II collagen are utilized.

Fibrillar collagens are particularly useful in the present invention due to the ease of which aggregated polymer formation can be controlled. Accordingly, by controlling the mixture or temperature of the various components of the matrix components, a variety of polymer densities and consistencies can be achieved. The fibrillar collagens, e.g., types I, II, and III, are secreted from collagen-producing cells as triple-helical procollagen molecules, and processed into collagen molecules (also called tropocollagen) by specific proteolytic enzymes outside the cell. The collagen molecules then aggregate into ordered polymers called collagen fibrils, in a process known as fibrillogenesis. This process is driven in part by the tendency of the molecules to self-assemble in vivo. The collagen fibrils themselves often aggregate to form collagen fibers reaching several microns in diameter.

Under the proper conditions, a solution of substantially monomeric collagen molecules will aggregate to form fibrils in vitro, with the fibrils themselves often assembling into a matrix, e.g., a gel. The aggregation state of collagen in solution, i.e., the extent to which collagen molecules are associated with one another to form fibrils, is affected by numerous factors. In particular, the aggregation state of collagen molecules is a function of the nature and concentration of the collagen molecules, the presence or absence of other macromolecules, e.g., proteoglycans ("PG") or glycosaminoglycans ("GAG"), time, temperature, and the nature of the solvent, e.g., pH, ionic strength, solute and solvent composition. See, e.g., Vies and Payne, in Collagen (M. E. Ninmi, ed.) vol. 1, pp. 114–138 (CRC Press), 1988 and Helseth and Vies, J. Biol. Chem. 256:7118, 1981. By adjusting these parameters, one skilled in the art can manipulate the aggregation state of collagen molecules. Conditions that result in a desired collagen aggregation state, or that cause controlled transitions from one aggregation state to another, can be determined by one skilled in the art without undue experimentation, i.e., through routine optimization of the desired parameters. Many of these parameters are readily amenable to being controlled by the concurrent flow methodologies of the present invention. For example, aggregation can be controlled by altering the concentration of collagen molecules in the solution, aggregation can be controlled by altering the concentration of non-collagen molecules in the solution, and aggregation can be controlled by altering the solute and/or solvent composition of the solution.

Condensing Agents

Condensing agents that are suitable for the use in the methods and apparatuses of the invention preferably comprise a DNA condensing domain and, optionally, a targeting ligand attachment domain. Ligands may be optionally attached to the condensing agent to improve cell targeting or transfection efficacy. DNA:condensing agent complexes comprising these condensing agents and made by the methods and apparatuses described herein are also specifically contemplated in one embodiment of the invention. Complexes can be in the form of a nucleic acid torus (e.g., a DNA torus), nucleic acid-lipid complexes or liposomes, emulsions, microemulsions and nucleic acid-containing viral or retroviral particles, to name a few examples. Suitable nucleic acid condensing domains or agents may comprise any molecule with cationic character and include, for example, polycationic molecules.

Polycationic molecules useful in the methods and apparatuses of the invention are exemplified by molecules including, for example, polycationic peptides or polypeptides; polycationic proteins; polycationic polyamino acids; polycationic carbohydrates; polycationic synthetic polymers; polycationic small synthetic organic amines; inorganic multivalent cations; cationic lipids; and synthetic viral particles. As noted previously, while the herein-described methods and apparatuses are especially useful for preparing condensation complexes, this is but one example of the invention's utility.

As noted previously, a variety of polycationic molecules are useful in the context of the present invention. Polycationic proteins and peptides that are suitable for use in the methods and apparatuses described herein are any protein or peptide possessing any degree of cationic character and include, for example, basic FGF and protamine. Polyamino acids that are suitable for use in the methods and apparatuses described herein include, for example, homopolymers and random copolymers of lysine and arginine or mimetics of polyamino acids of lysine and arginine. Polycationic carbohydrates that are suitable for use in the methods and apparatuses described herein include for example, chitosan, amine-containing polysaccharides, and the like.

Polycationic synthetic polymers that are suitable for use in the methods and apparatuses described herein include, for example, polymers comprising primary amine or other alkaline functional groups, and the like. Polyethylenimine and DEAE-dextran are examples of such polymers.

Polycationic small synthetic organic amines that are suitable for use in the methods and apparatuses described herein include, for example, spermine, spermidine, polybrene and the like. Multivalent inorganic cations that are suitable for use in the methods and apparatuses described herein include, for example, cobalt hexamine(III) and the like.

Other exemplary components of complexes that may be made using the methods and apparatuses disclosed herein include cationic lipids, which include those molecules comprising from about 4 to about 40 carbon atoms and one or more free amine groups that generally form micelles or liposomes in water. These include, for example, D- and L-cholesterol, cetyltrimethylammonium bromide (CTAB), and the like.

Synthetic viral particles and subunits thereof may also be used as condensing agents. Useful viral particles include both natural and synthetic types. For example, synthetic viruses are described in published International App. No. WO 96/41606; the disclosures of that application are incorporated by reference herein.

In a further embodiment, nucleic acid molecules can be condensed by a polycation such as protamine or chitosan in non-aqueous solutions such as dimethyl sulfoxide, tetramethyl urea, N,N-dimethylacetamide, and the like. Accordingly, in the various embodiments non-aqueous solvents can be utilized to formulate the molecular-entity containing solutions. For example, dimethyl sulfoxide and other solvents can be used to dissolve synthetic polymers for matrix formation as well as biomolecules such as protein (to be used as a targeting agent, as a carrier, or as a matrix formulation) and nucleic acids, and small organic molecules. Therefore, using non-aqueous solvents for the various solutions are considered within the context of all embodiments of the present invention. In one illustrative example, a nucleic acid containing solution can be controllably mixed with a condensing agent, both in DMSO, thereby forming a uniform colloidal dispersion. To this dispersion, a third non-aqueous solution containing a matrix component, for example, poly(lactic-co-glycolic acid) (PLGA) is introduced in controlled manner from a third reservoir.

The use of non-aqueous solutions as an alternative aspect of the present invention would therefore allow for the incorporation of water soluble nucleic acid condensates or other gene therapy vectors with water insoluble compounds in a solution form. Accordingly, the compositions generated by methodologies using non-aqueous solvents likely have increased stability due to the lack of water. In addition, the use of non-aqueous solvents provides added benefits in the context sterility as well as when utilizing formulations wherein water may act as a chaotrope and thereby causing a destabilizing effect on the composition.

Nucleic Acid: Condensing Agent Complexes

Maintaining a proper/desired ratio of the gene therapy vector to vehicle is important. This is especially true when using condensing formulations, as particle size may be tightly controlled.

First, maintaining the proper ratio of DNA and condensing agent throughout the introduction and mixing processes is important. The reaction of DNA and a polycationic condensing agent forms a condensation DNA:condensing agent complex by charge neutralization. This is known as a DNA condensation reaction. In a DNA condensation reaction product, the DNA minimally interacts with solvent and is considered to be compacted. It is typically achieved when the DNA and polycationic condensing agent are mixed at a charge ratio close to 1. As DNA is normally a negatively charged molecule and the condensing agent is normally a positively charged molecule, the stoichiometry may be predetermined based on the overall charge of the DNA:condensing agent complex relative to the summation of the charges of the DNA and condensing agent individually. A significant deviation from charge neutrality either lead to incomplete condensation or aggregation. Thus, it is desirable to control the mixing ratio of the DNA and condensing agent reaction by controlling the rate of introduction of the DNA and condensing agent such that a relative 1:1 charge ratio, or other suitable ratio if desired, of the two components is maintained during the entire course of mixing. If additional reactants are added, ratios are adjusted as appropriate.

Second, prevention of further reaction of the DNA:condensing agent complex with additional DNA (or higher order DNA:condensing agent complex) is also important. If further reaction of the newly-formed DNA:condensing agent complex is allowed to occur, aggregates of DNA:condensing agent complexes, or higher order DNA complexes, are formed. These larger-sized aggregates tend to have vastly different physical and functional properties from the small and non-aggregate condensation complexes. They in essence "contaminate" the product by introducing variably sized particles into the product mix and thus contribute to loss of particle size uniformity in condensation reaction products. This is deleterious in situations where the function or efficacy of the condensation complex is dependent on maintaining strict particle size and uniformity of the complex. Thus, it is desirable to prevent a mixing and co-existence of free DNA with DNA:condensing agent complex during the condensation reaction. The heterogeneity of such a complex, if it contains aggregates, may also affect the stability of the complex.

In one embodiment, the methods and apparatuses of the present invention, the control of the introduction rate and ratio of the DNA and condensing agent, the mixing of the reagents, and the separation of free DNA from already formed DNA complex of a desired size, which prevents subsequent aggregation, are accomplished simultaneously.

The concurrent flow mixing methods and apparatuses described herein allow the desired condensation reaction to occur while minimizing or preventing conditions for the aggregation side-reaction to occur. The introduction and mixing are controlled by calibrated introduction of solutions comprising the DNA and the condensing agent into the mixer such that only the optimal mixing ratio of DNA and condensing agent are continuously introduced into the mixing chamber and exit therefrom. This ensures a consistent production of the desired condensation complexes at an optimal charge ratio while minimizing or avoiding the formation of undesirable aggregation products.

The flow rate of the solution through the mixer is modulated by the rate of introduction of the solutions into the system; that is, the flow of the solutions through the mixer and out of the apparatus is dependent upon the combined flow rate of the DNA solution and the condensing agent solution being introduced. Because the condensation reaction occurs within microseconds upon interaction of the solutions, while the aggregation reaction requires a significantly longer time (seconds or longer), the flow rate is set such that the residence time of DNA and condensing agent in the mixer is long enough for a complete condensation reaction but not sufficient for aggregation. This is accomplished by effectively removing the DNA:condensing agent complex from the reaction system before it can encounter and aggregate with newly introduced additional DNA, thus avoiding formation of DNA:condensing agent aggregates and formation of non-uniform particles.

Thus, more homogeneous DNA:condensing agent complex products are produced consistently and reliably by the methods and apparatuses of the invention. The methods and apparatuses described herein are suitable for producing greater than 90% (w/w), alternatively greater than 95% (w/w), or alternatively greater than 98% (w/w) pure DNA:condensing agent condensation complexes relative to other DNA:condensing agent aggregate complexes or free DNA or condensing agent.

The DNA:condensing agent complexes produced by the methods and apparatuses of the invention may be collected and stored in a collecting or storage vessel attached to the apparatuses described herein, such as, for example, beakers, flasks, bottles, test tubes and the like. Such collecting or storage vessels may optionally comprise or be connected to an agitator, including an agitation means, such as a stirrer or shaker, in order to maintain the uniformity of the complex. The complexes may be stored as solutions or isolated in more concentrated forms, including for example, lyophilized particles.

The invention also relates to the complexes produced by the methods and apparatuses described herein. Such products are suitable to deliver genes into cells, particularly mammalian cells, for example, in order to regulate the operation and function of the cells or to provide a replacement or supplement for a defective or deficient gene product.

Molecular Entity Complexes and Compositions (Mixtures)

Molecular entities as used in regard to the methods and apparatuses described herein refer to any molecules that are capable of reacting, e.g., to form a gene therapy vector and vehicle mixture. Alternate embodiments of the invention include the methods and apparatuses disclosed herein wherein the first molecular entity is a nucleic acid and the second molecular entity is a condensing agent. Whereas, in other embodiments, the first molecular entity is another gene therapy vector such as virus or bacteriophage and the second molecular entity is a vehicle or targeting ligand (e.g., an anti-knob antibody-ligand construct for "re-targeting" adenovirus). In targeting formulations, it may be desirable to control the mixture of gene delivery vehicle and targeting ligand, in order to provide uniform consistency and scaleable methodology. Further, in other aspects, after combining the targeting ligand and the gene therapy vector it may be useful to uniformly mix this complex with a vehicle such as a pharmaceutically acceptable carrier or buffer or a biocompatible matrix formulation (see, WO 97/38729, incorporated herein by reference). In various embodiments, the nucleic acid is a therapeutic nucleic acid.

In an alternate embodiment of the invention, the aforementioned apparatuses further comprise: a) a first check valve attached to the first molecular entity-containing solution dispenser and the mixer; and b) a second check valve attached to the second molecular entity-containing solution dispenser and the mixer.

Yet another embodiment of the invention relates to the aforementioned apparatuses wherein: a) the first molecular entity containing-solution dispenser comprises a syringe having a Luer connector or an equivalent component attached to an exit tube, said exit tube being connected on the side opposing the Luer connector to an in-line check valve, said in-line check valve being attached on the side opposite the exit tube to a connecting tube and said connecting tube being attached on the side opposite said in-line check valve to said mixer; b) the second molecular entity containing-solution dispenser comprises a syringe having a Luer connector attached to an exit tube, said exit tube being connected on the side opposing the Luer connector to an in-line check valve, said in-line check valve being attached on the side opposite the exit tube to a connecting tube and said connecting tube being attached on the side opposite said in-line check valve to said mixer; c) the mixer is a static chaotic mixer connected to a removal exit tube; and d) wherein the solution flow controller is a syringe pump that controls the syringes in a) and b) above.

The invention also relates to a method adapted for the preparation of gene therapy condensates, compositions, and mixtures comprising two or more molecular entities, comprising the steps of: a) providing: i) a first molecular entity-containing solution; ii) a second molecular entity-containing solution; and iii) a flow-through mixer; and b) simultaneously introducing said first molecular entity-containing solution and said second molecular entity-containing solution, each in a controlled and independent manner, into said mixer such that the two solutions contact, mix, and form a mixed solution comprising the first and second molecular entity, such that said mixed solution exits from the flow-through mixer at a controlled rate, and wherein said first and second molecular entity-containing solutions independently comprise at least one gene therapy vector and at least one gene therapy vector vehicle. This method may optionally further comprise the step of: c) isolating the resulting first molecular entity and second molecular entity composition from the resulting mixed solution.

The methods and apparatuses described herein are suitable for providing molecular entity condensation complexes of any uniform particle size depending on flow. The preferable size of which can be manipulated by controlling solution flow is about 2000 nm or smaller. For example, complexes can be formed having a particle size of about 2000 nm or smaller, alternatively of about 500 nm or smaller, alternatively of about 200 nm or smaller, alternatively of about 100 nm or smaller, or alternatively of about 50 nm or smaller. The methods described herein are also suitable for providing condensation complexes in a range of particle sizes, including for example, from about 30 to about 2000 nm, alternatively from about 30 to about 500 nm, or alternatively from about 30 to about 200 nm, or alternatively of from about 30 to about 100 nm. The condensation complexes are produced by the methods and apparatuses described herein at a suitable, predetermined particle size not only to facilitate reaching their target, but also to avoid their removal from the blood by the reticuloendothelial system prior to reaching their target.

In various embodiments of the disclosed invention, the first or second (or third, etc.) molecular entity may comprise a gene therapy vector (e.g., naked nucleic acid, virus, bacteriophage, etc.), and the other molecular entity (or entities) may comprise a vehicle (e.g., a condensing agent, pharmaceutical acceptable carrier, matrix formulations, etc.).

In one embodiment, the present invention relates to an apparatus for preparing complexes and compositions of a predetermined size and/or uniform composition comprising: a) a first molecular entity-containing solution dispenser; b) a second molecular entity-containing solution dispenser; c) a mixer (static or dynamic) attached to a solution removal outlet, wherein the first molecular entity-containing solution dispenser and the second molecular entity-containing solution dispenser are each independently connected to the mixer; and d) a solution flow controller that independently controls the rate of introduction of the first molecular entity-containing solution and the second molecular entity-containing solution into the mixer, thereby controlling the size and/or uniform composition of the first molecular entity and second molecular entity composition or complex formed thereby and the rate of flow of the resulting mixed solution through the mixer and out to the solution removal outlet. A general schematic of an embodiment of an apparatus according to the invention is illustrated in FIG. 1.

The methods and apparatuses of the invention may be utilized and carried out as batch processes or in a continuous process. In a batch process, the process is halted so that new reagents may be loaded into their respective dispensers, including introduction means such as syringes, reservoirs, and the like. In a continuous process, the each reagent is continuously fed into an individual auxiliary dispenser in communication with its respective dispenser connected (directly or indirectly) to the mixer whereby it is unnecessary to halt operation of the process to load new reagents into the system. In one embodiment, the apparatus of the invention is a flow-through apparatus for continuously preparing a mixture of uniform consistency or of a predetermined size. In another embodiment, the methods of the invention utilize a flow-through apparatus for continuously preparing a mixture of uniform consistency or a condensation complex of a predetermined size.

For the methods and apparatuses described above, the flow-through mixer may comprise: a) a controllable first molecular entity-containing solution dispenser; b) a controllable second molecular entity-containing solution dispenser; c) a removal outlet; and d) a chamber to receive delivery of solution from both dispensers a) and b) such that both solutions delivered by said solution dispensers will co-mix and flow through the removal outlet c). In various embodiments, the flow-through mixer above may comprise: a) a controllable DNA-containing solution dispenser and b) a controllable condensing agent-containing solution dispenser. One example of a flow-through mixer is an in-line mixer. The dispenser may be any dispensing means or device suitable for dispensing a liquid in a controlled manner including, for example, syringes, reservoirs, tanks, bottles or any solution introducing means.

In one exemplary embodiment, provided for illustrative purposes, the apparatus may be applicable to laboratory scale mixtures as illustrated in FIG. 3. For example, the preparation of a DNA-containing condensate is described herein. The DNA-containing solution is introduced via introduction means, syringe 1 and the condensing agent-containing solution is introduced via introduction means, syringe 10. The rate of addition, and thus flow rate of the solutions through the apparatus, is controlled by controlling means, such as by syringe size and/or via syringe pump 11. The syringe pump may be a dual stage pump, wherein both syringes may be independently or dependently controlled or multiple pumps may be employed, each controlling a single syringe. In various preferred embodiments, the flow rate of the reactants is the same for each reactant.

The term "syringe" as used herein refers to a plunger and body assembly with an outlet and appropriate connection fitting. The syringes may be made of glass or an inert polymer, i.e., polyethylene, polypropylene and the like, and have Luer lock, slip tip or other equivalent fittings. While syringes that contain volumes from about 1 to about 250 mL are available and suitable for use in these apparatuses, those containing volumes from about 1 to about 20 mL are more suitable for applications on this scale. Such syringes are commercially available and are exemplified by those available from Becton Dickinson (Franklin Lakes, N.J.).

The syringe Luer lock fittings are attached to Luer lock Connector 2 (female/male) which may be optionally attached to in-line check valve 3. The in-line check valve 3 is useful for keeping dead volume as small as possible in the system and is designed for placement in a flow system in order to limit fluid transfer to one direction, thus eliminating any possible back-flow of fluid. In-line check valves suitable for use in the apparatus and methods described herein are available from various commercial vendors including, for example, Upchurch Scientific (Oak Harbor, Wash.). The check valve 3 is then attached to tubing 8, such as PEEK polyether ketone resin tubing, TYGON, LDPE, TEFLON or other suitable tubing, which is attached to mixing means 6. The tubing carries the solutions through the system and must be inert to the reagents and conditions of the condensation procedure.

The tubing should be of a suitable diameter to achieve the necessary flow rate throughout the system and should also keep dead volume in the system to a minimum. Suitable tubing is typically from about 0.0025 to about 0.055 inches inside diameter for applications on this scale. In one embodiment, the tubing is 0.02 inches inside diameter and is about 2 to about 3 inches long. The tubing is attached to Luer connect adapter 2, or optionally in-line check valve 3, by flangeless nuts with ferrules 4, such as those available from Upchurch Scientific. The tubing is also attached to mixing means 6 by Fingertight III fittings 5 (available from Upchurch Scientific) with ferrules or the like.

Suitable mixing means 6 should allow for sufficient residence time and mixing for the DNA:condensing agent condensation complex, the homogenous mixture, and/or the gene therapy vector:targeting ligand complex to form, yet allow for removal of the desired product from the system prior to further reaction. The static mixing means may be "chaotic", that is, comprising numerous channels, capillaries, passages, or the like disposed in divergent and alternately changing directions for the solution to flow through. These paths may diverge and re-converge once or a plurality of times in order to provide turbulence and mixing of the incoming solutions.

Enhanced mixing is achieved when the "dead volume" in the static mixer and connections is minimal. For example, in a mixing tee such as the U-466 static mixing tee available from Upchurch Scientific, the dead volume should be about 3.1 µL or less to ensure adequate mixing. Enhanced mixing is also achieved when the mixer volume to surface area ratio is relatively low. Enhanced mixing in a mixer such as the U-466 is achieved using a solution flow rate (combined flow rate of all solutions introduced into the mixer) from about 0.5 to about 3.0 mL/minute. A filter aid, such as UHMWPE, available from Upchurch Scientific, for example, may also enhance mixing.

Static mixing means suitable for use on this scale are exemplified by the static mixing tee available from Upchurch Scientific. The static mixing means ideally comprises Fingertight Universal fittings or the like for ease of operation and should be made of a material inert to the condensation conditions, such as PEEK or similar materials. Enhanced mixing is achieved when the "dead volume" in the dynamic mixer and connections is minimal. Dynamic mixing means suitable for use in the methods and apparatuses disclosed herein are exemplified by the in-line mixers such as the Mixer 6.0 ml and Mixer 0.6 ml models available from Amersham Pharmacia Biotech (Piscataway, N.J.).

The product is removed from the mixing means by flow of the solution through the mixing means and leaves the mixing means via an exit tube 9, which in these types of applications is typically a length of tubing as described above, which may be attached by way of Fingertight III fitting 7 with ferrules or the like. The product may be collected and stored in solution "as is." Alternatively, the complex mixture may be collected and stored in a more concentrated solution or exchanged into an alternate solution, or it may be isolated and stored in an alternate form (e.g., lyophilized).

While discussed in the context of DNA:condensing agent condensations, the methods and apparatuses described herein are amenable to condensation of any suitable molecular entities, particularly in situations where condensation-aggregation differentiation effects are present. Similarly, the methods described herein, which utilize flow-through apparatuses, may be used to prepare a variety of admixtures, such as to continuously prepare a DNA:condensing agent condensation complex of a predetermined size.

Small Scale Applications

The methods and apparatuses described herein are suitable for use in laboratory tests and experiments, including in vivo and in vitro studies. For example, the methods and apparatuses may be used to prepare compositions, complexes, and condensates (as used herein such terms can collectively be referred to as mixtures, products, or resulting compounds) for investigation of physicochemical characteristics (i.e., structural or physical property measurements) of such compounds. These studies include, for example, spectroscopic (e.g., X-ray, infrared, ultraviolet, and nuclear magnetic resonance, and the like) studies, chromatographic (e.g., liquid, gas, electrophoresis, and the like) studies, and microscopic and other physical measurements (e.g., particle size, particle stability, particle or mixture uniformity, morphology and the like). Through such studies, the stability of particles over variety of conditions (i.e., time, temperature, storage conditions), the degree of aggregation of particles under various process conditions, shelf life and retention of physicochemical characteristics may be analyzed. The particles produced by the methods and apparatuses described herein may also be analyzed by various techniques including, for example, laser light scattering, electrospray mass spectrometry, polydispersion index, electron microscopy, circular dichroism, and the like. The laser light scattering evaluation method is utilized in Example 2 for a DNA:condensing agent condensation complex comprising plasmid DNA (pSVβ) and FGF-polylysine conjugate.

The methods and apparatuses may also be used to prepare complexes and mixtures for investigation of their functional properties. Such studies include, for example, in vitro studies of degree of cell transfection of the complexes, specificity of cell targeting of complexes, and expression efficacy of the delivered complex. Where the expression product is a unique marker capable of detection (i.e., by immunochemical methods, fluorescence, staining or the like), the complexes made using the methods and apparatuses described herein may be used as in vitro or in vivo diagnostic agents, e.g., to detect for specific cell types, or may comprise a marker such as a radiolabel (e.g., isotope of iodine or phosphorus) or radioactive emitter, which is useful for determining distribution or location of the complex in specific cell types.

The methods and apparatuses described herein are also suitable for preparation and administration of complexes and mixtures useful as therapeutic agents. For example, the apparatuses described herein may be used for direct or "bedside" preparation and administration of an appropriate gene therapy vector. In such an application, the removal means of the flow-through mixing apparatus may be a tube that is connected to an injection needle suitable for subcutaneous, intracutaneous, intravenous, intramuscular, intraarticular, intrasynovial, intrasternal, intrathecal, intralesional, intracranial injection or infusion, or other similar type administration of the condensation complex to the patient, or piggybacked to an infusion tubing for co-administration with other drugs or therapeutic or nutritional agents as pharmaceutically acceptable solutions. The apparatus provides controlled, consistent administration of the complex and minimizes introduction of operator variability, which may be particularly suitable for certain administration methods where complex or mixture integrity over time, temperature or other storage or delivery conditions is an issue. This type of administration of the mixtures or complexes allows for administration of freshly prepared products and avoids problems associated with deterioration of a mixture or condensation complexes due to storage and particle size variability induced by prolonged periods between preparation and administration of the complex.

The methods and apparatuses described herein for use in preparation and direct administration of mixtures or complexes of gene therapy vectors and/or vehicles may conveniently comprise syringes as solution introduction means and syringe pumps (including programmable pumps) to control the flow rate of the solutions. For example, the syringes, connecting tubing, connectors, mixer and needle may be made of inert materials appropriate for delivery of therapeutic agents to a human patient, including appropriate degrees of sterility. Such materials are described herein and are also known to those of ordinary skill in the medical device arts.

The complexes and other admixtures prepared as disclosed herein may include other solutions and molecular entities, as noted above. Pharmaceutically acceptable solutions for introduction of the appropriate molecular entities in such an application are those suitable for administration with the complex and/or mixture or are an integral component of the mixture, for example, directly into a human patient, and include, for example, water, with an optional buffer composition where appropriate. Other such pharmaceutically acceptable solutions include those comprising compositions, carriers, diluents and reagents suitable for pharmaceutical administration.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the significant production of undesirable physiological effects such as nausea, dizziness, gastric upset and the like.

The preparation of a pharmacological composition that contains active ingredients dispersed therein is well understood in the art. Typically, such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. As disclosed herein, the methods and apparatuses of the present invention are useful in preparing, processing and administering any of the herein-disclosed compositions, as well as many others described in the art.

Industrial Scale Applications

The methods and apparatuses of the invention are also amenable to large-scale preparation. The methods and apparatuses described herein control the production of the desired mixtures and condensation complexes by controlling the reaction parameters. Thus, scaling the process up from milliliter to liter and larger sized processes is dependent on maintaining such control. The elements described in the exemplary laboratory scale example above may be substituted with suitable devices that provide equivalent operation on a larger scale. The parameters (i.e., relative size of syringes, tubes and mixer, flow rates, dead volume, and the like) described for the laboratory scale apparatus above are indicative of the parameters that should be proportionally maintained to attain mixtures and complexes of the desired physical characteristics and uniformity on a larger scale.

The method or apparatus may be scaled up by utilizing tanks or reservoirs for the solution introduction means, one for the first molecular entity (gene therapy vectors) (e.g., nucleic acid, virus, bacteriophage, etc.)) containing solution and one for the second molecular entity (e.g., vehicles) solution. The tanks may be made of any material that is inert to the reactants and solvents and suitable for the reaction conditions. Such tanks may be made from, for example, metal, stainless steel, ceramic composite, glass, polymer, and the like. They may also be lined or coated with an inert material if necessary. The tanks will comprise or be associated with one or more controllable pumps that allow for independent control of the rate of introduction of each solution in order to insure appropriate mixing, residence time in the mixer and removal of the solution and the product. The tanks also comprise an outlet means, which may be attached directly, or via an in-line check valve, to the mixer.

The connections between tanks and the mixer may comprise pipes or tubing comprising metal, stainless steel, polymer, i.e., polyethylene or polypropylene, or other suitable material. The connecting pipes or tubing must be inert to the solutions and conditions of the condensation reaction and must be of a length and diameter to provide the necessary flow rate and pressure to ensure an appropriate level of mixing of the solutions and in the context of condensation reactions, subsequent removal of the resulting complex before any further aggregation may occur in the reaction chamber. They may be attached and connected by appropriate fasteners, ferrules and O-rings or the like to ensure a tight fit between connections and prevent leakage.

The mixer, including the mixing chamber, must be of a suitable material such as those described for the solution introduction tanks above. The material must be essentially inert to the reaction conditions and preferably resistant to corrosion. It must also be of a size and shape to facilitate proper mixing and flow of solution through the chamber. The residence time and flow rate are dependent, in part, on the size and construction of the mixer, including the mixing chamber. The volume/surface area ratio must also be maintained in a suitable range in order to achieve appropriate mixing or condensation of complex particles of the desired uniformity and size. This ratio should be relatively low in order to attain desirable results. The mixer may have a plurality of inlets and outlets in order to ensure appropriate mixing and removal of the solution into and out of the chamber. In such instances, each inlet may be singly or multiply associated with one or more controllable pumps and solution introduction means. Each outlet means may be separately or multiply associated with one or more collection means.

The mixer may comprise any form of agitation suitable for ensuring complete mixture of the reactants. A static mixer is a mixer that does not rely on mechanical agitation, shaking or stirring by a mechanical device in the mixer. Rather, a mixer, relies on walls, channels, capillaries, barriers, offset plates or protrusions such as rods or nubs, any of which may comprise holes or openings, or be offset from one another, to direct the flow path in a way to provide flow turbulence and mixing of the solutions as they proceed through the mixer. In such a case, the flow rate and pressure is determined by a number of factors, including for example, the flow rate of each solution being introduced, the size and diameter of the connectors and inlet and outlet openings in each component, the size and shape of the chamber, the volume to surface area ratio of the mixer, the number of flow paths and flow path diversions in the mixer and the like. The mixer may comprise a tee configuration or a serpentine configuration.

A dynamic mixer is any mixer that provides agitation and mixing of the solutions therein by application of mechanical forces, for example, agitation by movement of a paddle or blade connected to an external power source, such as a motor. In such instances, the mixing of the solutions is accomplished by the rotation of the paddle or blade, which creates the turbulence necessary for mixing. Because dynamic mixers typically accommodate larger volumes, they may be suitable for larger scale operations. The dynamic mixers appropriate for use in the methods and apparatuses disclosed herein should comprise materials (e.g., stainless steel, glass, polyethylene) which are essentially inert to the condensation reaction conditions. Such materials are used in the areas of the mixer where the solutions contact the mixer.

The above-mentioned components may also require independent temperature sensors and controls. While the smaller scale reaction is run essentially at room temperature and the thermal conditions of the reaction do not significantly impact the result of condensation reactions or molecular entity mixing on a smaller scale. For example, there may be a more significant impact of exothermic energy produced during the condensation reaction when operating at larger volumes. Further, when using matrices as a vehicle it may be optimal to control the temperature of the matrix material. If necessary, the solutions prior to and/or during introduction may be heated or cooled to ensure proper reaction temperatures in the mixing chamber. This may be done by either an external (i.e., temperature control of the tank or reservoir by external application of heating/cooling) or internal i.e., heat addition or removal by a means heating or cooling means disposed inside the tank) means.

The methods and apparatuses of the invention may be used in batch processes or in continuous processes. In a batch process, the process is halted so that new reagents may be loaded into their respective introduction means, i.e., syringe, or reservoir and the like. In a continuous process, the reagents are continuously fed into an intermediate introduction means whereby it is unnecessary to halt operation of the process for loading new reagents into the system.

Solvents or diluents suitable for use in the methods and apparatuses described herein are those in which the molecular entities are soluble and those which are appropriate for product formation. The solvents or diluents should be essentially inert to the reaction apparatus, conditions, reagents and products and preferably enhance formation of the desired mixture or condensation complexes. For in vivo applications, the solvents utilized are preferably essentially non-toxic to the cell type being targeted, including, for example water. The solutions employed may optionally comprise suitable additives, such as buffers, surfactants, and the like, where appropriate.

Condensing agents useful in the methods and apparatuses described above include any molecule that is capable of condensing with or bringing about the compaction of a nucleic acid. The choice of the condensing agent will be partially dependent on the nature of the molecule selected to be targeted by the DNA:condensing agent complex, i.e., the appropriate condensing agent should have the ability to conjugate or associate with the target molecule. This may be via covalent or non-covalent association. Suitable condensing agents used in the methods described herein should also demonstrate limited toxicity or be non-toxic. The condensing agent should also be sufficiently positively charged per molecule to provide the desired overall charge in the DNA-:condensing agent complex.

The methods and apparatuses described above are suitable for providing a DNA:condensing agent condensation complex having an essentially neutral charge, for example, a complex comprising a one to one ratio of DNA to condensing agent assuming the magnitude of the DNA negative charge is roughly equivalent to the magnitude of the positive charge of the condensing agent. In general, slightly-positively charged DNA:condensing agent complexes are more stable than negatively-charged or completely neutral complexes. Thus, one embodiment of the invention relates to methods described above utilizing an excess of condensing agent relative to the amount of DNA employed. Alternate embodiments relate to methods wherein the relative amounts of condensing agent and DNA used are such that the condensing agent/DNA charge ratio is from about 1 to about 5, alternatively from about 1 to about 2.5, alternatively from about 1 to about 2, or alternatively from about 1.0 to about 1.5.

Numerous types of molecules are known to bind specific receptors on cells and they are suitable for use as a part of the gene therapy and vehicle products formed by the herein-disclosed methods and apparatuses. Such molecules include those that are often identified in the art as "ligands."

Ligands suitable for use in the methods and apparatuses described herein include any peptide or polypeptide that has the ability to bind the target cell and be internalized. Any protein, polypeptide, analogue, or fragment that binds to a cell-surface receptor and is internalized may be used. These ligands may be produced by recombinant or other means in preparation for conjugation to the nucleic acid binding domain. The DNA sequences and methods to obtain the sequences of these receptor-binding internalized ligands are well known. For example, useful ligands include those recited in published International App. No. WO 96/36362, the disclosures of which are incorporated by reference herein.

Additional Agents

The complexes and mixtures made by the methods and apparatuses of the invention often comprise a nucleic acid and a condensing agent. They may also comprise other agents or molecules necessary to enhance the ability of the complex to effect the desired modification of the cell function generally. These additional agents may also enhance specifically, for example, the stability of the complex under the reaction conditions, the targeting specificity of the complex, and/or the ability of the complex to internalize into the targeted cell. Such additional agents or molecules may be covalently or non-covalently bound to the complex or simply added to the admixture. One example of such an agent includes, for example, linking agents.

A linker may be used in the methods and apparatuses described herein to conjugate to either the condensing agent or the DNA. As used herein, a "linker" is a chemical or peptide capable of interacting with a condensing agent or DNA. Typically, the linker is attached to the condensing agent prior to the condensation reaction, in which case the condensing agent-linker conjugate is condensed with the DNA. Useful linkers are known in the art; see, e.g., published International App. No. WO 96/36362, the disclosures of which are incorporated by reference herein.

Imaging agents may also be suitable for use in the methods and apparatuses described herein and include those that are capable of being a marker for diagnostic purposes. Examples of such agents include DNA reporter genes, such as genes expressing luciferase or β-galactosidase, and β- or γ-emitters, such as $P^{32}$, $H^3$, $I^{125}$ or $I^{131}$ attached to DNA or the condensing agent. Such radiolabels are useful for investigation of biodistribution of the condensation complexes. These agents are also useful for the study of organ distribution uptake using scintigraphy imaging techniques to follow the distribution of the emitters.

Gene Therapy Vector and Vehicle Compositions

The condensation complexes described herein are preferably of uniform particle size, including, for example, complexes having a particle size of about 2000 nm or smaller, alternatively, complexes having a particle size of about 500 nm or smaller, alternatively of about 200 nm or smaller, alternatively of about 100 nm or smaller, or alternatively of about 50 mn or smaller. The condensation complexes are those in a range of particle sizes, including for example, for about 30 to about 2000 nm, alternatively from about 30 to about 500 nm, alternatively from about 30 to about 200 nm, from about 100 to about 200 nm, or alternatively of from about 30 to about 100 nm. The condensation complexes may also be of a suitable particle size to avoid removal from the blood by the reticuloendothelial system prior to reaching their target and may be useful for transfecting DNA into a mammalian cell. The gene therapy vector and vehicle products formed by the methods and apparatuses described herein may be utilized in pharmaceutical compositions, as noted previously.

In other aspects, the present invention provides for a method adapted to the uniform mixing of a gene therapy vector and a vehicle. Accordingly, as noted above, the present invention provides a scalable methodology adapted specifically for forming uniform compositions of gene therapy vectors and vehicles.

The gene therapy vector and vehicle products formed by the methods and apparatuses described herein may also be administered directly, e.g., directly from the apparatus into a subject for nucleic acid delivery to that subject as part of a therapeutic treatment regimen, or they may be isolated and administered at a later time. Such administration may be parenterally, orally, by inhalation, topically, rectally, or buccally. Parenteral use includes subcutaneous, intracutaneous, intravenous, intramuscular, intraarticular, intrasynovial, intrastemal, intrathecal, intralesional, and intracranial injection or infusion techniques. Preferred modes of administration depend upon the indication treated. Dermatological and ophthalmologic indications will typically be treated locally whereas other indications will typically be treated by systemic, intradermal, or parenteral modes of administration.

The gene therapy vector and vehicle products formed herein may be formulated into pharmaceutical compositions suitable for various applications as noted above. Time-release formulations are also desirable. Effective concentrations of one or more of the products are mixed with a suitable pharmaceutical carrier. As used herein an "effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

The concentrations or amounts of the gene therapy vector: vehicle mixtures that are effective requires delivery of an amount, upon administration, that ameliorates the symptoms or treats the disease. Typically, the compositions are formulated for single dosage administration. Therapeutically effective concentrations and amounts may be determined empirically by testing the complexes in known in vitro and in vivo systems, such as those described here; dosages for humans or other animals may then be extrapolated therefrom.

The gene therapy vector and vehicle mixture is included in the pharmaceutically acceptable carrier in an amount sufficient to exert a therapeutically useful effect in the absence of undesirable side effects on the patient treated. The compositions may be delivered as pharmaceutically acceptable salts, esters or other derivatives of the compositions and may be readily prepared by those of skill in this art using known methods for such derivatization. Preferably, compositions made using the methods and apparatuses disclosed herein may be administered to animals or humans without substantial toxic effects. It is understood that the number and degree of side effects depends upon the condition for which the complexes are administered. For example, certain toxic and undesirable side effects are tolerated when treating life-threatening illnesses, such as tumors, that would not be tolerated when treating disorders of lesser consequence. The concentration of gene therapy vector: vehicle in the composition will depend on absorption, inactivation and excretion rates thereof, the dosage schedule, and amount administered as well as other factors known to those of skill in the art.

Preferably, the gene therapy vector: vehicle mixtures used in the compositions described herein is substantially pure. As used herein, "substantially pure" means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance.

The compositions may be formulated for local or topical application, such as for topical application to the skin and mucous membranes, such as in the eye, in the form of gels, creams, and lotions and for application to the eye or for intracistemal or intraspinal application. Such solutions, particularly those intended for ophthalmic use, may be formulated as 0.01%–10% isotonic solutions, pH about 5–7, with appropriate salts. The ophthalmic compositions may also include additional components, such as hyaluronic acid.

The compositions may be formulated as aerosols for topical application (see, e.g., U.S. Pat. Nos. 4,044,126, 4,414,209, and 4,364,923). Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

Upon mixing or addition of the composition with a carrier, the resulting mixture may be a solution, suspension, emulsion or the like. The form of the resulting mixture depends upon a number of factors, including the intended mode of administration and the solubility of the gene therapy vector vehicle in the selected carrier. The effective concentration is sufficient for ameliorating the symptoms of the disease, disorder or condition treated and may be empirically determined based upon in vitro and/or in vivo data, such as the data from the mouse xenograft model for tumors, rabbit ophthalmic model, or wound models.

The gene therapy vector and vehicle compositions may be formulated for local or topical application, such as for topical application to the skin and mucous membranes, such as in the eye, in the form of gels, creams, and lotions and for application to the eye. Such solutions, particularly those intended for ophthalmic use, may be formulated as 0.01%–10% isotonic solutions, pH about 5–7, with appropriate salts. Suitable ophthalmic solutions are known (see, e.g., U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The compositions may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponge (see, e.g., U.S. Pat. Nos. 3,956,044 and 4,045,238), that has been soaked in the composition and that releases the composition upon contact with tissue. In addition, the compositions may be formulated with other bio-compatible matrices, including, for example, PLGA, methylcellulose, carboxymethylcellulose, collagen, and the like, a number of which are described in published International Patent App. No. WO 97/38729. The compositions may also be applied in pellets (such as Elvax pellets (ethylene-vinyl acetate copolymer resin); about 1–5 μg of conjugate per 1 mg resin).

In order that the invention be more fully understood, the following examples are set forth. These examples are for the purpose of illustration only and are not to be construed as limiting the scope of the invention in any way.

EXAMPLES

Example 1

Plasmid DNA (pSVβ):FGF-polylysine (FGFK) Condensation Complexes Prepared by Fast Addition and Concurrent Flow Mixing Method Complexation between plasmid DNA pSVβ and FGF-polylysine conjugate (FGFK), which is a good example of DNA: polycationic condensing agent, follows a cooperative kinetics model, i.e., a rate of a higher order aggregation of existing pSVβ:FGFK condensates (complex particles) always exceeds the rate of formation of such complex particles. This cooperativity kinetics makes the generation of small and uniform condensates very challenging. For a therapeutic DNA complex, control of the condensate particle size is essential for consistent transgene activity.

Figure 3:
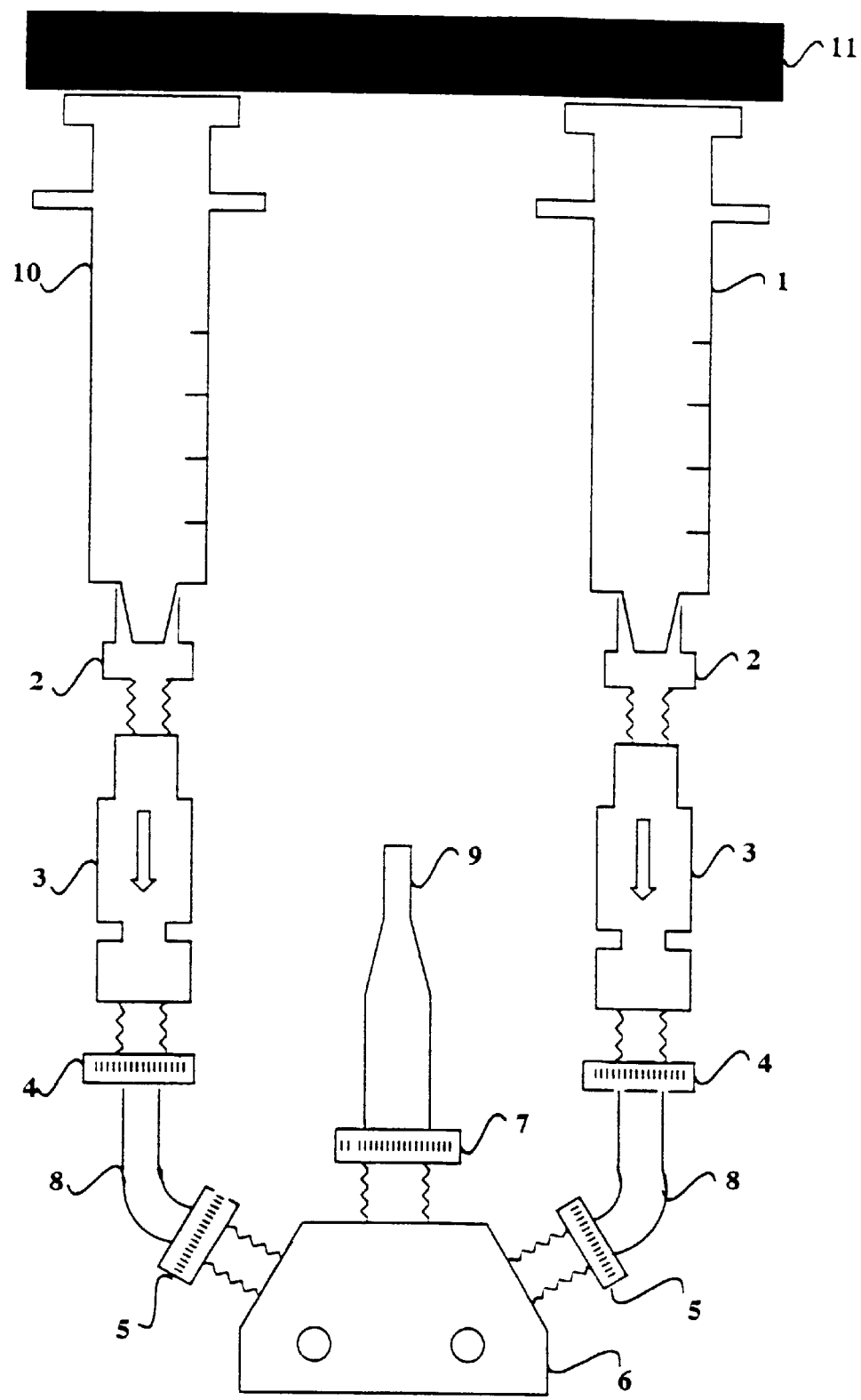
FIG. 3 is a schematic of an embodiment of a laboratory scale apparatus.

Complexes of plasmid DNA pSVβ and FGF-polylysine conjugate (FGFK) were prepared using the following two addition/mixing methods: (1) fast addition of a pSVβ solution into an FGFK solution; and (2) concurrent flow mixing of pSVβ and FGFK solutions using the flow-through mixer device as illustrated in FIG. 3.

Both methods were designed to discourage the cooperative aggregation process which leads to large particles. The fast pSVβ addition method presumably accomplishes this by shortening the exposure time of free pSVβ molecules to existing pSVβ:FGFK condensates during addition and mixing. The concurrent flow mixing method would remove the pSVβ:FGFK condensates right after they are formed and direct them away from the reaction environment (e.g., the interior of the mixer), thereby eliminating the chance for high order aggregation.

The first method, which involves a fast addition of a pSVβ stock solution into an FGFK stock solution, is described in Example 1A. The second method, the concurrent flow mixing method (see, e.g., FIG. 3), is described in Example 1B. Laser light scattering measurement was employed to determine the average hydrodynamic diameter and size uniformity of the pSVβ:FGFK condensates in both Examples 1A and 1B.

Example 1A

Plasmid DNA (pSVβ): FGF-polylysine (FGFK) Condensation Complexes Prepared by Fast Addition Method A pSVβ plasmid DNA (4.8 kb) solution at 1.4 mg/mL in 10 M TE (Tris-EDTA) buffer (pH 7.4) was diluted to a concentration of 0.1 mg/mL with NANOPURE water to make Reaction Solution #1. An FGF2-Polylysine conjugate (FGFK) solution (0.5 mg/mL in 10 mM HEPES buffer solution, pH7.0) was diluted to a concentration of 0.1 mg/mL with NANOPURE water to make Reaction Solution #2.

Both Solution #1 and Solution #2 were filtered through 0.2 μM filters (AERODISC; Gelman Sciences, Ann Arbor, Mich.). Reaction Solution #1 was placed in a Becton-Dickinson 5 mL polypropylene syringe. This solution was added to the Reaction Solution #2 by a syringe pump at a rate of 5 mL/min. This addition was operated in a batch mode where each batch is made of 0.5 mL of each Reaction Solution #1 and #2. These two solutions were mixed in the receiving vessel by a magnetic stir bar rotating at ~80 RPM. (For example, one may use an auto-stirrer such as a VWR Model 205 Auto-Stirrer.)

Eight (8) batches were prepared and each batch was analyzed by using a laser light scattering (LLS) instrument (Malvern Zetasizer 3000) for determination of particle size (Table 1). The instrument conditions used were as follows: sample cell: quartz rectangular fluorescence cell with 10 mm path length; incubation: 10–15 min. at 23° C.; detection angle: 90°; and wavelength: 480 nm. The data collected are set forth in Table 1 below.

| Batch | KCPS | $Z_{Ave}$ | Polydispersity |
|-------|------|-----------|----------------|
| 1 | 8.0 ± 0.3 | 53.7 ± 7.6 | 0.225 ± 0.128 |
| 2 | 13.5 ± 0.8 | 61.5 ± 10.3 | 0.268 ± 0.270 |
| 3 | 16.4 ± 0.5 | 59.7 ± 3.1 | 0.250 ± 0.064 |
| 4 | 13.9 ± 0.4 | 66.0 ± 10.1 | 0.284 ± 0.264 |
| 5 | 15.3 ± 0.4 | >3000* | n/a |
| 6 | 14.7 ± 0.3 | >3000 | n/a |
| 7 | 14.7 ± 0.7 | >3000 | n/a |
| 8 | 16.6 ± 0.4 | 68.1 ± 12.8 | 0.249 ± 0.159 |
| 8** | 26.6 ± 1.1 | 80.8 ± 9.1 | 0.137 ± 0.120 |

*Aggregated with average particle size exceeded the upper limit of the instrument (3000 nm).
**measured after being stored for 23° C. for 12 hours In Table 1, KCPS values represent the scattering light intensity detected from each sample; a higher KCPS (or intensity) is generally indicative of larger and/or more particles. $Z_{AVE}$ is a measure of the average hydrodynamics diameter in nanometers. Polydispersity is a measure of the uniformity of particle size distribution of the product.

The results in Table 1 suggest that although small particles of pSVβ:FGFK condensate (<100 nm) were occasionally obtainable by the fast addition method, this method is highly likely to yield inconsistent and unreliable results. For example, among the 8 batches prepared, three were highly aggregated with $Z_{ave}$>3000 nm. The particles generated by this method also appeared to be less stable with a continued growth in particle size observed when stored at room temperature.

Example 1B

Plasmid DNA (pSVβ): FGF-polylysine (FGFK) Condensation Complexes Prepared by Concurrent Flow Mixing Method A pSVβ plasmid DNA (4.8 kb) solution at 1.4 mg/mL in 10 M TE buffer (pH 7.4) was diluted to a concentration of 0.1 mg/mL with NANOPURE water to make Reaction Solution #1. An FGF2-Polylysine conjugate (FGFK) solution (0.5 mg/mL in 10 mM HEPES buffer solution, pH 7) was diluted to a concentration of 0.1 mg/mL with NANOPURE water to make Reaction Solution #2. Both Solution #1 and Solution #2 were filtered through an 0.2 μM filter (AERODISC; Gelman Sciences, Ann Arbor, Mich.). Each Reaction Solution was placed in a Becton-Dickinson 5 mL polypropylene syringe.

All the remaining components of the flow-through mixer device were assembled as depicted in FIG. 3. The device was first flushed with 10 mL of NANOPURE water using two Becton-Dickinson 5 mL polypropylene syringes. The flushing syringes were then replaced with the syringes containing Reaction Solution #1 and #2. The syringe pump was set at a flow rate of 1.0 mL/min. The initial 300 μL of eluent was discarded. The syringe pump was set at a batch mode with delivery volume of 0.25 mL from each syringe per batch. The total batch size collected was 0.5 mL.

Three 0.5 mL batches were collected in 2 mL polypropylene vials each with a 9 mm magnetic stir bar rotating at a slow rate (setting "2" using a VWR Model 205 Automatic Stirrer) (Batches 1–3 in Table 2). Another 3 batches (0.5 mL) were received in the same 2 mL vials without the stir bar or any other mixing means (Batches 4–6 in Table 2). Each batch run was then analyzed using a Laser Light Scattering instrument (Malvern Zetasizer 3000) for determination of particle size (Table 2). The following instrument conditions were used: sample cell: quartz rectangular fluorescence cell with 10 mm path length; incubation: 15–45 min. at 23° C.; detection angle: 90°; and wavelength: 480 nm.

TABLE 2

| Batch | KCPS | $Z_{Ave}$ | Polydispersity | Stirring in Receiving Vessel |
|-------|------|-----------|----------------|------------------------------|
| 1 | 33.6 ± 0.5 | 98.4 ± 6.8 | 0.208 ± 0.077 | Yes |
| 2 | 31.9 ± 0.6 | 98.0 ± 11.0 | 0.186 ± 0.093 | Yes |
| 3 | 31.1 ± 0.2 | 109.8 ± 38.3 | 0.239 ± 0.094 | Yes |
| 3* | 33.6 ± 0.46 | 100.1 ± 14.0 | 0.210 ± 0.141 | Yes |
| 4 | 54.6 ± 0.3 | 143.4 ± 11.8 | 0.262 ± 0.070 | No |
| 5 | 45.3 ± 0.3 | 140.4 ± 13.0 | 0.204 ± 0.128 | No |
| 6 | 58.1 ± 0.5 | 131.0 ± 13.5 | 0.241 ± 0.044 | No |
| 6* | 62.0 ± 0.6 | 147.8 ± 20.0 | 0.204 ± 0.093 | No |

*measured after being stored at 23° C. for 12 hours

In Table 2, KCPS values represent the scattering light intensity detected from each sample, a higher KCPS (or intensity) is generally indicative of larger and/or more particles. $Z_{AVE}$ is a measure of the average hydrodynamic diameter in nanometers. Polydispersity is a measure of the uniformity of particle size distribution of the product. The results in Table 2 suggest that (1) stirring in the receiving vessel further decreases size, (2) excellent batch to batch reproducibility in terms of particle size and size uniformity, (3) formation of uniform particles, (4) low probability for aggregation aggregation was not seen), and (5) DNA:condensing agent complex particles maintain the $Z_{AVE}$ size and size uniformity for at least 12 hours at 23° C.

Example 2

Evaluation of Particle Size and Gene Expression

Generally, receptor binding and internalization may be measured by various methods. One method involves competitive inhibition assay of the complex to cells expressing the appropriate receptor, in order to demonstrate receptor binding.

A second method of evaluating receptor binding and internalization involves measuring expression of a reporter gene such as β-gal (e g., enzymatic activity) in cells that have been transformed with a complex of a plasmid encoding a reporter gene and a conjugate of a receptor-binding internalized ligand and nucleic acid binding domain. This assay is particularly useful for optimizing conditions to give maximal transformation. Thus, the optimum ratio of receptor-binding internalized ligand/nucleic acid binding domain to nucleic acid and the amount of DNA per cell may readily be determined by assaying and comparing the enzymatic activity of β-gal.

As such, these first two assays are useful for preliminary analysis. Failure to show receptor binding or β-gal activity does not per se eliminate a candidate receptor-binding internalized ligand/nucleic acid binding domain conjugate or fusion protein from further analysis, however. A third method is preferred for use when the targeted therapeutic agent is a cytotoxin. This third method involves a cytotoxicity assay performed on cells transformed with a cytocide-encoding agent linked to a receptor-binding internalized ligand/nucleic acid binding domain.

In general, while any cytocidal molecule may be used, ribosome inactivating proteins are described herein as exemplary. Saporin, a type I ribosome inactivating protein, is used herein as a more specific example. A statistically significant reduction in cell number demonstrates the ability of the receptor-binding internalized ligand/nucleic acid binding domain conjugate or fusion to deliver nucleic acids into a cell. Any cell expressing the appropriate receptor may be used. For FGF as a ligand, cell lines including COS and rabbit smooth muscle cells may be used.

In this example, DNA:condensing agent condensation of pSVβ and FGFK84 is performed as follows. The DNA condensation is carried out at a final concentration of 50 μg/mL DNA and 100 μg/mL FGFK84 in 5% mannitol. For 1 mL condensation mixtures, 50 μg pDNA (0.7–3.5 mg/mL) is added to an appropriate amount of 10% mannitol (USP) and water mixture to give a final mannitol concentration of 5% in a microfuge tube. 100 μg of FGFK84 (1.4 mg/Ml) is then added to the same tube followed by gentle pipetting up and down 3–5 times. The condensation mixture is incubated at room temperature for 1 hr whereupon may they are suitable for use in the gene expression assay. The particle sizes are monitored by laser light scattering after delivery to the cells.

The resulting particles are then analyzed for their ability to transfect and induce gene expression in the following assay:

The media are aspirated from the cells and washed once with sterile dPBS. Pre-warmed trypsin-EDTA is added to the cells. An equivalent volume of BHK media is added to a 15 mL conical tube, whereupon the trypsin cell suspension is added and the cells are spun at 1500 rpm for 5–7 minutes at room temperature. The media from the pellet is aspirated and re-suspended in BHK media. A small aliquot of the cell suspension is removed to determine the cell concentration using a hemacytometer. The number of wells in a 24 well plate that are needed for the assay are calculated: 9 wells per sample or positive control and 3 wells for negative control. The number of BHK cells for the assay are calculated: 15,000 cells per well, 1.5 mL of media per well. The cells are then seeded in a 24 well plate and incubated for 24 hr. in 5% $CO_2$ at 37° C.

The volume of condensate needed to deliver 2.5, 2.0, and 1.5 μg plasmid DNA is calculated. For example, where the concentration of plasmid DNA in the condensate is 50 μg/mL and it is desired to add 2.5 μg of plasmid DNA, then 0.050 (2.5 μg÷50 μg/mL) mL of condensate per well need be added. This amount is added to triplicate wells. Additional triplicate wells are also mock infected with BHK media to serve as negative controls. After the condensate is added to the wells, centrifuge the plates at 1200 g (2500 rpm) for 45 minutes at 28° C. The plates are then incubated for 72 hr.in 5% $CO_2$ at 37° C.

The media is then aspirated from the cells and washed once with room temperature dPBS. 200 μL of 0.2% Triton lysis buffer is added to each well and rotated vigorously for 10–15 minutes at room temperature. The lysates are transferred to 1.5 mL microcentrifuge tubes and are centrifuged at 13,500 g for 2–3 minutes at 4° C. The supernatant is assayed for reporter gene activity and total protein concentration. The mean condensate activity is calculated as mU b-gal or pg luc/mg total protein/μg input DNA.

Figure 4:
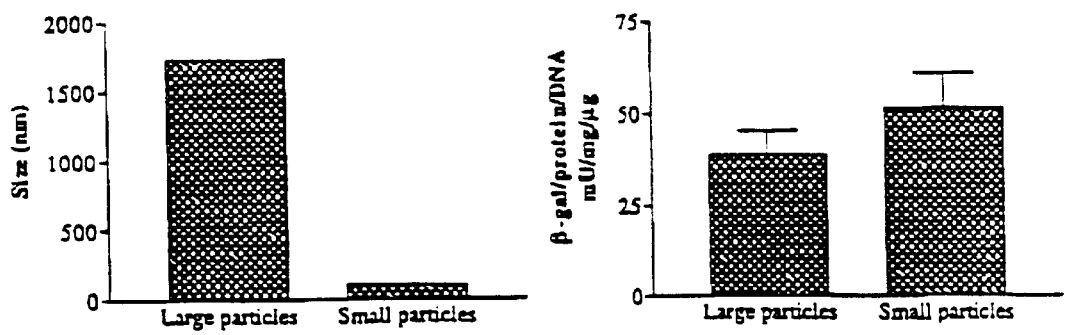
FIG. 4 is a graph of a comparison of DNA:condensate particle size and gene expression under different ionic conditions.

As illustrated in FIG. 4, the DNA:condensing agent condensation complexes of small particle size (about 100 nm or less) possessed at least equal or greater ability to be internalized and induce production of an expression product as the DNA:condensing agent condensation complexes of large particle size (about 2000 nm or less).

Numerous modifications may be made to the foregoing system without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow.

What is claimed is:

1. A method for the preparation of a homogenous mixture comprising two or more molecular entities, comprising:
   concurrently and separately introducing at least a first molecular entity-containing solution and a second molecular entity-containing solution, each in a controlled and independent manner, into at least a first flow-through mixer such that the two solutions contact, mix, and form the homogenous mixture, such that said homogenous mixture exits from the flow-through mixer at a controlled rate, and wherein said first and second molecular entity-containing solutions collectively comprise at least one vector and at least one vehicle; wherein said vehicle is selected from the group consisting of a ligand, a polycation, and a matrix formulation.

2. The method of claim 1, wherein the mixer is a static mixer.

3. The method of claim 1, wherein the mixer is a dynamic mixer.

4. The method of claim 1, further comprising concurrently introducing a third molecular entity-containing solution.

5. The method of claim 1, further comprising a second flow-through mixer, wherein the second flow-through mixture allows for the introduction of a third and/or fourth molecular entity-containing solution into the uniform mixture.

6. The method of claim 1, wherein at least one molecular entity-containing solution comprises a medium that consists essentially of a non-aqueous medium.

7. The method of claim 6, wherein the non-aqueous medium is selected from the group consisting of dimethylsulfoxide, tetramethyl urea, and N,N-dimethylacetamide.

8. The method of claim 6, wherein the non-aqueous medium is mixed with an aqueous medium to form a uniformly mixed product.

9. The method of claim 1, wherein the vehicle is a matrix formulation.

10. The method of claim 1, wherein the vehicle is a polycation.

11. The method of claim 1, wherein said flow-through mixer comprises:
   a) a controllable first molecular entity-containing solution dispenser;
   b) a controllable second molecular entity-containing solution dispenser;
   c) a removal outlet; and
   d) a chamber to receive delivery of solution from both dispensers a) and b) such that both solutions delivered by said solution dispensers will co-mix and flow through the removal outlet c).

12. The method of claim 1, wherein the vector is a nucleic acid and the vehicle is a condensing agent.

13. A method of preparing uniform size particles comprising a DNA:condensing agent condensation complex of a predetermined size, comprising the steps of:
   a) providing i) a DNA-containing solution, ii) a condensing agent-containing solution, and iii) a flow-through mixer; and b) concurrently and separately introducing said DNA-containing solution and said condensing agent-containing solution, each in a controlled and independent manner, into said mixer such that the two solutions contact, mix, and form a mixed solution containing a DNA:condensing agent condensation complex of predetermined size thereby, and such that said condensation complex exits from the flow-through mixer at a controlled rate such that further reaction of said condensation complex with additional DNA- and/or condensing agent-containing solution is avoided.

14. The method of claim 13, wherein the mixer is a static mixer.

15. The method of claim 13, further comprising the step of:

c) isolating the condensation complex from the mixed solution.

16. The method of claim 13, wherein said flow-through mixer comprises:

a) a controllable DNA-containing solution dispenser;

b) a controllable condensing agent-containing solution dispenser;

c) a removal outlet; and d) a chamber to receive delivery of solution from both dispensers a) and b) such that both solutions delivered by said solution dispensers will co-mix and flow through the removal outlet c).

17. The method of claim 13, wherein said condensing agent comprises a polycationic molecule.

18. The method of claim 17, wherein said polycationic molecules are selected from the group consisting of polycationic peptides, polycationic carbohydrates, polycationic synthetic polymers, inorganic multivalent cations, and synthetic viral particles.

19. The method of claim 13, wherein the amounts of condensing agent and DNA used are such that the condensing agent/DNA charge ratio is from about 1 to about 5.

20. The method of claim 13, wherein the condensation complex has a particle size of about 2000 nm or smaller.

21. The method of claim 13, wherein the condensation complex has a particle size of about 1000 nm or smaller.

22. The method of claim 13, wherein the condensation complex has a particle size of about 500 nm or smaller.

23. The method of claim 13, wherein the condensation complex has a particle size of about 200 nm or smaller.

24. The method of claim 13, wherein the condensation complex has a particle size of about 100 nm or smaller.

25. The method of claim 13, wherein the condensation complex has a particle size of about 30–200 nm.

26. The method of claim 13, wherein the condensation complex has a particle size of about 30–100 nm.

27. A method for the preparation of a homogenous mixture comprising two or more molecular entities, comprising:

concurrently and separately introducing at least a first molecular entity-containing solution and a second molecular entity-containing solution, each in a controlled and independent manner, into at least a first flow-through mixer such that the two solutions contact, mix, and form the homogenous mixture, such that said homogenous mixture exits from the flow-through mixer at a controlled rate; and isolating a resulting first molecular entity and second molecular entity composition from the resulting homogenous mixture, wherein said first and second molecular entity-containing solutions collectively comprise at least one vector and at least one vehicle; wherein said vehicle is selected from the group consisting of a ligand, a polycation, and a matrix formulation.

28. A method for the preparation of a homogenous mixture comprising two or more molecular entities, comprising:

concurrently and separately introducing at least a first molecular entity-containing solution and a second molecular entity-containing solution, each in a controlled and independent manner, into at least a first flow-through mixer such that the two solutions contact, mix, and form the homogenous mixture, such that said homogenous mixture exits from the flow-through mixer at a controlled rate, and wherein said first and second molecular entity-containing solutions collectively comprise at least one vector and at least one vehicle; wherein said vector is a virus and said vehicle is a matrix formulation.

* * * * *

UNITED STATES PATENT AND TRADEMARK OFFICE
CERTIFICATE OF CORRECTION

PATENT NO. : 6,537,813 B1
DATED : March 25, 2003
INVENTOR(S) : Xian Chen et al.

It is certified that error appears in the above-identified patent and that said Letters Patent is hereby corrected as shown below:

Title page,
Item [56], under OTHER PUBLICATIONS should read -- Davis et al., "A Simple, Reliable Rapid-Mixing Apparatus for Continuous-Flow Studies," *Analytical Biochemistry* 97:428-437, 1979. --.

Column 37,
Line 34, after "synthetic polymers," should read -- spermidine, polybrene, --.

Signed and Sealed this

Second Day of September, 2003

JAMES E. ROGAN
*Director of the United States Patent and Trademark Office*